United States Patent
Di Tullio et al.

(10) Patent No.: US 10,234,450 B2
(45) Date of Patent: Mar. 19, 2019

(54) ELECTROCHEMICAL METHODS AND DEVICES FOR AMENDING URINE SAMPLES FOR IMMUNOSENSOR DETECTION

(71) Applicant: Abbott Point of Care Inc., Princeton, NJ (US)

(72) Inventors: Katrina Di Tullio, Stittsville (CA); G. Bruce Collier, Fitzroy Harbour (CA); John Lewis Emerson Campbell, Woodlawn (CA)

(73) Assignee: Abbott Point of Care Inc., Princeton, NJ (US)

( * ) Notice: Subject to any disclaimer, the term of this patent is extended or adjusted under 35 U.S.C. 154(b) by 144 days.

(21) Appl. No.: 15/472,553

(22) Filed: Mar. 29, 2017

(65) Prior Publication Data

US 2017/0199181 A1    Jul. 13, 2017

Related U.S. Application Data

(62) Division of application No. 14/206,532, filed on Mar. 12, 2014, now Pat. No. 9,651,547.

(60) Provisional application No. 61/781,576, filed on Mar. 14, 2013.

(51) Int. Cl.
| | | |
|---|---|---|
| *C12Q 1/58* | (2006.01) | |
| *G01N 33/543* | (2006.01) | |
| *G01N 33/68* | (2006.01) | |
| *G01N 33/62* | (2006.01) | |

(52) U.S. Cl.
CPC ......... *G01N 33/54306* (2013.01); *C12Q 1/58* (2013.01); *G01N 33/5438* (2013.01); *G01N 33/54393* (2013.01); *G01N 33/62* (2013.01); *G01N 33/6893* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 4,954,087 | A | 9/1990 | Lauks et al. |
| 5,006,309 | A | 4/1991 | Khalil et al. |
| 5,063,081 | A | 11/1991 | Cozzette et al. |
| 5,089,424 | A | 2/1992 | Khalil et al. |

(Continued)

FOREIGN PATENT DOCUMENTS

WO    2011159707 A1    12/2011

OTHER PUBLICATIONS

"Non-Final Office Action" issued in U.S. Appl. No. 14/206,532, dated Jan. 12, 2016, 14 pages.

(Continued)

*Primary Examiner* — Erik B Crawford
(74) *Attorney, Agent, or Firm* — Kilpatrick Townsend & Stockton LLP

(57) ABSTRACT

The present invention is directed to methods and devices for amending undiluted and partially diluted urine samples in a manner suitable for performing immunoassays for target analytes, for example NGAL. Generally, the urine sample is treated with reagents including at least one of buffer materials, water soluble proteins, urease, and other interferent mitigants. These reagents control the pH of the urine sample in a manner suitable for immuno-binding reactions and ameliorate interferences, particularly during the detection step.

16 Claims, 13 Drawing Sheets

(56) References Cited

U.S. PATENT DOCUMENTS

| | | |
|---|---|---|
| 5,096,669 A | 3/1992 | Lauks et al. |
| 5,141,868 A | 8/1992 | Shanks et al. |
| 5,200,051 A | 4/1993 | Cozzette et al. |
| 5,514,253 A | 5/1996 | Davis et al. |
| 5,554,339 A | 9/1996 | Cozzette et al. |
| 5,821,399 A | 10/1998 | Zelin |
| 6,030,827 A | 2/2000 | Davis et al. |
| 6,824,985 B1 | 11/2004 | Rheinheimer et al. |
| 7,419,821 B2 | 9/2008 | Davis et al. |
| 7,682,833 B2 | 3/2010 | Miller et al. |
| 7,723,099 B2 | 5/2010 | Omakor et al. |
| 7,732,099 B2 | 6/2010 | Ogata et al. |
| 7,960,132 B2 | 6/2011 | Nakaminami et al. |
| 8,084,272 B2 | 12/2011 | Omakor et al. |
| 8,309,364 B2 | 11/2012 | Miller et al. |
| 2003/0170881 A1 | 9/2003 | Davis et al. |
| 2004/0018577 A1 | 1/2004 | Emerson Campbell et al. |
| 2005/0054078 A1 | 3/2005 | Miller et al. |
| 2006/0160164 A1 | 7/2006 | Miller et al. |
| 2007/0131548 A1 | 6/2007 | Winarta et al. |
| 2009/0170143 A1 | 7/2009 | Uttenthal et al. |
| 2009/0176274 A1 | 7/2009 | Tu et al. |
| 2010/0167301 A1 | 7/2010 | Collier et al. |
| 2010/0227775 A1 | 9/2010 | Birkenmeyer et al. |
| 2011/0028562 A1 | 2/2011 | Marona et al. |
| 2011/0287455 A1 | 11/2011 | Venge et al. |
| 2012/0034684 A1 | 2/2012 | Campbell et al. |
| 2012/0295290 A1 | 11/2012 | Campbell et al. |
| 2013/0343955 A1 | 12/2013 | Doyle et al. |
| 2014/0271368 A1 | 9/2014 | Hofmann et al. |
| 2014/0273014 A1 | 9/2014 | Di Tullio et al. |
| 2014/0273034 A1 | 9/2014 | Di Tullio et al. |
| 2017/0023565 A1 | 1/2017 | Di Tullio et al. |

OTHER PUBLICATIONS

"Non-Final Office Action" issued in U.S. Appl. No. 14/206,532, dated Aug. 10, 2016, 9 pages.

"Notice of Allowance", issued in U.S. Appl. No. 14/206,532, dated Feb. 8, 2017, 9 pages.

"Non-Final Office Action", issued in U.S. Appl. No. 14/206,831, dated Jan. 12, 2016, 15 pages.

"Notice of Allowance", issued in U.S. Appl. No. 14/206,831, dated Jul. 21, 2016, 8 pages.

Bahr, et al., "Urea as a Selective Inhibitor of Human Tissue Alkaline Phosphatases", Clinica Chimica Acta 17, 1967, pp. 367-370.

Birkett, et al., "Action of Urea on Human Alkaline Phosphatases: with a Description of Some Automated Techniques for the Study of Enzyme Kinetics", Arch. Biochem, Biophys 121, 1967, pp. 470-479.

Cuckle, et al., "Measurement of Activity of Urea Resistant Neutrophil Alkaline Phosphatase as an Antenatal Screening Test for Down's Syndrome", BMJ,301, 1990, 1024-1026.

Dawson, et al , "Data for Biological Research", 3rd Ed., Clarendon Press, Oxford, 1996, p. 555.

Denier, et al., "Kinetic Comparison of Tissue Non-Specific and Placental Human Alkaline Phosphatases Expressed in Baculovirus Infected Cells: Application to Screening for Down's Syndrome", BMC Biochemistry, 3(2)1, 2002, 8 pages.

Devarajan, "Review: Neutrophil Gelatinase-Associated Lipocalin: a Troponin-like Biomarker for Human Acute Kidney Injury", Nephrology 15, 2010, 419-428.

Gorman, et al., "Clinical Usefulness of Alkaline Phosphatase Isoenzyme Determinations", Clin. Biochem 10(5), 1977, pp. 171-174.

Jung, et al., "Describe instability of ALP due to pH extreme and other characteristics of urine", Clinica Chemica Acta, 131, 1983, 185-191.

Metz, et al., "The Inhibitory Effect of the Urea-Urease System on Human Tissue Alkaline Phosphatases," Clinica Chimica Acta 30, 1970, pp. 325-330.

Perlzweig , "The Activation of Urease", Science, vol. 76, 1976, 435-436.

Rajagopalan, et al. , "Competitive Inhibition of Enzyme Activity by Urea", JBC 236, 1961, pp. 1059-1065.

Xu and Ding , "N-Terminal Sequence and Main Characteristics of Atlantic Salmon (Salmo solar) Albumin", Preparative Biochemistry & Biotechnology, 35, 2005, 283-290.

Youle, et al., "Albumin Storage Proteins in the Protein Bodies of Castor Bean", Plant Physiol, 61:13-16, 1978.

Ziebig, et al., "Renal Elimination of Troponin T and Torponin I", Clinical Chemistry 49, 2003, 1191-1193.

Non-Final Office Action issued in U.S. Appl. No. 15/286,909, dated Aug. 16, 2018, 7 pages.

"Notice of Allowance" dated Nov. 7, 2018, issued in U.S. Appl. No. 15/286,909, 12 pages.

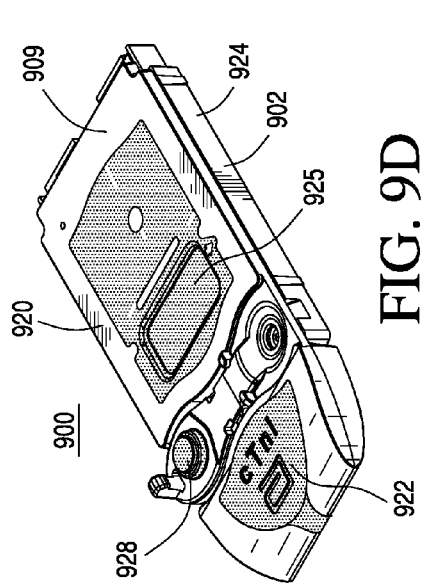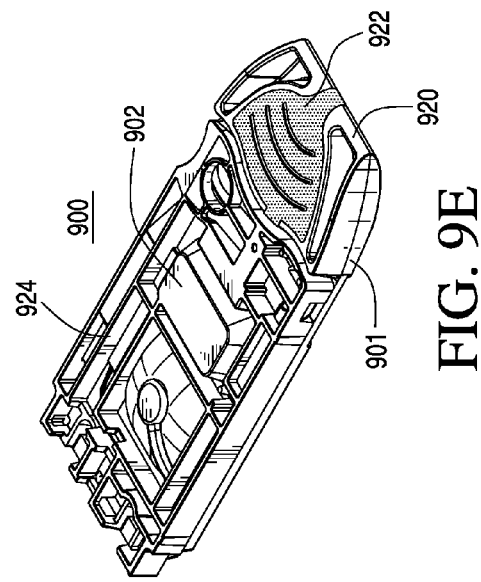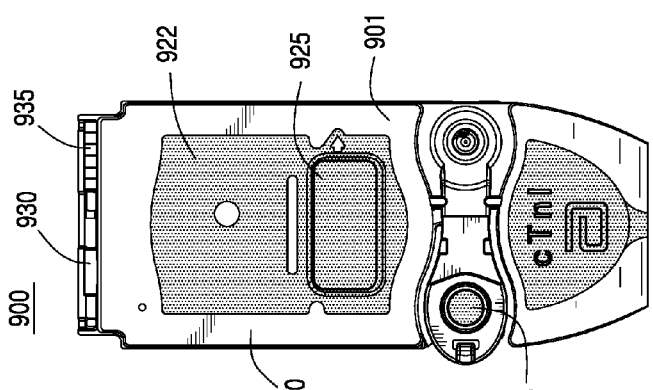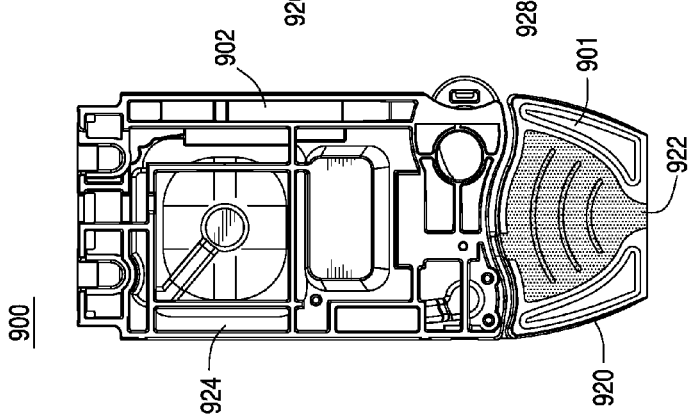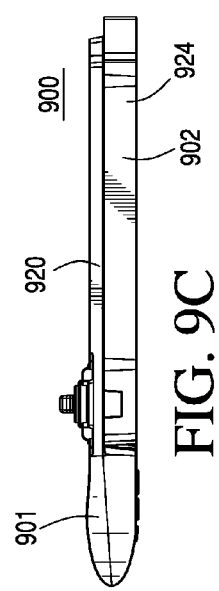

ELECTROCHEMICAL METHODS AND DEVICES FOR AMENDING URINE SAMPLES FOR IMMUNOSENSOR DETECTION

CROSS REFERENCE TO RELATED APPLICATIONS

This application is a Divisional Application of U.S. patent application Ser. No. 14/206,532 filed on Mar. 12, 2014, which claims priority to U.S. Provisional Application No. 61/781,576 filed on Mar. 14, 2013, the entireties of which are incorporated herein by reference.

FIELD OF THE INVENTION

The invention relates to analytical testing devices and methods for performing electrochemical immunoassays. Specifically, the invention relates to analytical testing devices and methods for performing electrochemical immunoassays on urine samples, and in particular using point of care immunoassays for testing for analytes in urine samples.

BACKGROUND OF THE INVENTION

Clinical analyses are generally performed in blood or derivates thereof (e.g., serum and plasma). Additionally, some clinical analyses are performed in urine, for example home pregnancy tests for human chorionic gonadotropin (hCG). However, urine typically comprises urea, which is synthesized as part of the urea cycle as a vehicle for the excretion of excess nitrogen. Urea is a known denaturant of proteins (e.g., enzymes), which are conventionally used in clinical analyses such as enzyme-linked immunosorbent assays (ELISA). Consequently, urine comprising urea generally presents a problem for clinical analyses (i.e., urea may cause the denaturation of the enzymes used in the clinical analyses), and there are currently no known solutions to overcome the potential denaturation of the proteins used in the clinical analyses.

Nonetheless, as clinical analyses evolve there is a desire to expand on clinical analyses performed in urine. For example, historically, a marker such as serum creatinine has been used to diagnose acute kidney injury (AKI). However, serum creatinine measurements may be influenced by muscle mass, muscle metabolism, gender, race, hydration status and medications. Additionally, the delay (e.g., up to 2-3 days after injury) and unreliability in serum creatinine rise may result in delayed diagnosis, which can translate to irreversible kidney damage prior to treatment. Therefore, the disadvantages of measuring serum creatinine for clinical purposes have necessitated the identification of novel early kidney injury markers. One such marker is neutrophil gelatinase-associated lipocalin (NGAL), which may be present in urine and/or plasma.

NGAL was identified as a secreted protein from granules of activated human neutrophils. See Devarajan, "Review: Neutrophil gelatinase-associated lipocalin: A troponin-like biomarker for human acute kidney injury," *Nephrology* 15 (2010) 419-428. Specifically, NGAL is a 25-kDa lipocalin that exists in monomeric and homo- and heterodimeric forms, the latter as a 46-kDa dimer with human neutrophil gelatinase. Lipocalins possess many different functions, such as the binding and transport of small hydrophobic molecules, nutrient transport, cell growth regulation, and modulation of the immune response, inflammation, and prostaglandin synthesis. Specifically, the NGAL protein is believed to bind small lipophilic substances such as bacteria-derived lipopolysaccharides and formylpeptides, and may function as a modulator of inflammation.

Renal injuries or disease, such as AKI, can result from a variety of different causes (such as illness, acute injury, sepsis, and radiocontrast nephropathy). NGAL may be utilized as an early marker for identifying AKI, as it is produced by nephrons and renal tubular cells in response to different types of injury in both animal and human models. Specifically, it has been proposed that NGAL plays an important role in renal protection, regeneration, and repair. For example, NGAL levels rise in acute tubular necrosis from ischemia or nephrotoxicity, even after mild "subclinical" renal ischemia, as compared to normal serum creatinine levels, which further substantiate the recognition of NGAL as an early renal injury marker. Moreover, NGAL is known to be expressed by the kidney in cases of chronic kidney disease and this is suggested to be predictive of disease stage. It has also been suggested that the degree of NGAL expression may distinguish amongst AKI, prerenal azotemia, and chronic kidney disease. Additionally, NGAL has been successful in predicting clinical outcomes in several common clinical scenarios. For example, in the future, NGAL may be used to expedite the drug development process or perhaps act as a safety marker during clinical trials of potentially nephrotoxic agents.

NGAL is rapidly secreted into the urine, where it can be easily detected and measured, and precedes the appearance of other known urinary or serum markers of ischemic injury. The protein is resistant to proteases, suggesting that it can be recovered in the urine as a faithful marker of tubule expression of NGAL. Further, NGAL derived from outside of the kidney, for example, filtered from the blood, does not appear in the urine, but rather is quantitatively taken up by the proximal tubule.

A variety of immunoassays are known in the art for detecting NGAL. For example, WO2010058378A1 outlines the immunoassay measurement of NGAL to diagnose AKI and the like and reports on the relative amounts of monomeric, dimeric, and heterodimeric NGAL to more accurately reflect disease. Further, Antibody Shop A/S describes a kit and components for the detection of NGAL (WO2006066587A1). United States Patent Application No. 2010/0227775 ('775) (Birkenmeyer et al. entitled: Immunoassays and kits for the detection of NGAL) discloses NGAL immunoassay methods and kits in which samples, e.g., blood, plasma, serum, and urine, suspected of containing human NGAL monomer and human NGAL dimer are contacted with at least one first antibody (e.g., a capture antibody) to form a first antibody/human NGAL complex. The at least one capture first antibody binds to human NGAL and is an antibody (e.g., a capture antibody) selected from the group consisting of an antibody produced by murine hybridoma cell line 1-2322-455 having ATCC Accession No. PTA-8024 and an antibody produced by murine hybridoma cell line 1-903-430 having ATCC Accession No. PTA-8026. Additionally, United States Patent Application No. 2009/0176274 discloses a recombinant human NGAL (rhNGAL) that can be employed as calibrator or control in an NGAL immunoassay. Determining the concentration of NGAL antigen in a test sample can be adapted to a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

While troponin assays (cardiac troponin I (cTnI) and cardiac troponin T (cTnT)) are not performed in urine in standard clinical analysis, at least one study has investigated these tests in urine, albeit with assays not specifically formatted for this sample type. See, e.g., Zeibig et al., Renal elimination of troponin T and troponin I: Clinical Chemistry 49, 1191-3, 2003.

The '775 application also discloses that these assays, kits, and kit components can be employed in other formats, for example, on electrochemical or other hand-held or point-of-care assay systems, e.g., The present disclosure is, for example, applicable to the commercial Abbott Point of Care (i-STAT®, Abbott Laboratories) electrochemical immunoassay system that performs immunoassays. Immunosensors and their methods of manufacture and operation in single-use test devices are described, for example in, U.S. Pat. No. 5,063,081, U.S. Patent Application Publication No. 2003/0170881, U.S. Patent Application Publication No. 2004/0018577, U.S. Patent Application Publication No. 2005/0054078, and U.S. Patent Application Publication No. 2006/0160164, which are incorporated in their entireties by reference for their teachings regarding same.

The i-STAT® immunoassay platform employs calf intestinal alkaline phosphatase [3.1.3.1] on the detection antibody in order to convert a substrate (p-nitrophenylphosphate) into an electrogenic species (p-nitrophenol), detectable on an amperometric biosensor. The pH optimum for the ALP reaction is 9.1. Using blood as the biological test specimen with ALP does not impose a residual matrix effect on the system. However, using urine may be problematic especially considering interfering elements like urea (average 0.4M, pH 4-5), pH (range 4.5-8.5; Jung et al., describe instability of ALP due to pH extreme and other characteristics of urine, Clinica Chimica Acta 131, 185-91, 1983; they also suggest to measure the pH of the test reaction and use this information during ALP activity calculations) and electroactive species (B vitamins, ascorbic acid etc.). Specifically, these elements can reduce enzymatic activity as well as increase background current generated during oxidation of species during analysis in the i-STAT® platform. As the current i-STAT® immunoassay cartridge in some embodiments may not include a full wash step after antigen is captured (instead the cartridge may be configured to perform a limited wash step), the ALP reaction is only partially cleared of potentially interfering elements from the original urine sample. As urea is commonly used as a biomolecular denaturant, it is anticipated that an enzyme such as ALP may be denatured in the presence of urine in the i-STAT® cartridge. Indeed, urea inhibition of ALP activity is well known and is used as a means of differentiating ALP isoenzymes (Bahr et al., Clinica Chimica Acta 17, 367-70, 1967).

The mechanism of inhibition is believed to be through a noncompetitive pathway, up to a threshold of urea concentration (Rajagopalan et al, JBC 236, 1059-65, 1961). Past this reversible inhibitive concentration, urea then becomes an irreversible denaturant (Birkett et al., Arch. Biochem. Biophys. 121, 470-9, 1967). ALPs from different tissue sources have been shown to have different susceptibility to the effect of urea, with the placental enzyme being the most resistant and the bone-derived version being the most sensitive (Birkett et al, 1967; Gorman and Statland, Clin. Biochem. 10, 171-4, 1977). Interestingly, Metz et al. (Clinica Chimica Acta 30, 325-30, 1970) showed that the inhibitory action of urea on ALP activity was markedly increased by pre-incubation with urease, and the effect was enhanced by prolongation of the pre-incubation period. Metz proposed that this effect was due to an increase in ammonium salts, especially at the reaction pH of 9.3 (ALP optimum pH 9.1). Further, production of ammonium leads to an increase in pH, potentially compounding the effect (Dawson, R. M. C., Elliott, D. C., Elliott, W. H. and Jones, K. M. (1986) Data for Biochemical Research, 3rd Edn., Clarendon Press, Oxford, p. 555). No further adjustment of the reaction to reverse the effect of the urease enhancement of urea inhibition on ALP was attempted.

U.S. Pat. No. 6,824,985 teaches the use of excess urea (>225 mM urea) in urine-based immunochromatographic strip and plate assays in order to reduce or eliminate bias in the test due to varying urea concentrations between biological samples. Another group employing an optical system, which monitors turbidity due to agglutination, teaches that urease can be added to the immunoassay to ensure antibody/antigen aggregation is generated independent of the concentration of urea (see, e.g., U.S. Pat. No. 7,960,132). However, neither of these teachings could be applied to the i-STAT® cartridge since a variable amount of urea may remain during the analysis cycle (limited wash after antigen capture) and the production of ammonium ions and increased pH, upon addition of urease would have to be addressed in order to prevent further inhibition of the ALP reaction.

One other consideration for carrying out an immunoassay in urine is the reduced ability of urine to naturally act as an immunoassay blocker (to reduce background) due to the low level of protein (0-8 mg/dL) compared to blood (6.3-8.2 g/dL). Additionally, the i-STAT® system has a limited capability of pretreating and conditioning the sample (e.g., use of buffers to adjust pH) as well as washing during the assay cycle in ways akin to the ARCHITECT® system (see, e.g., U.S. Patent Application Publication No. 2011/028562)

Based on the foregoing, there remains a need for pretreating or suitably amending substantially undiluted urine samples in a manner to reduce interferences and ensure immuno-binding reactions occur reliably, for measurements of various markers including NGAL and others, such as, *Chlamydia, Legionella*, various infectious disease agents, and various drugs of abuse (DOA). The present disclosure seeks to provide methods of pretreating or suitably amending urine samples and reaction steps in ways that are amenable to immunoassays using a device or system, e.g., the i-STAT® system. As well, other objects, advantages and inventive features, will become apparent form the detailed description provided herein.

SUMMARY OF THE INVENTION

In one embodiment, the present invention is directed to a device configured to perform an immunoassay for a target analyte in a urine sample. The device includes a first region comprising reagents configured to amend the urine sample. The reagents may comprise a water soluble protein and a buffer. The device further includes a second region comprising at least one electrode configured to determine a concentration of the target analyte in the amended urine sample. The first region is configured to provide a dissolved concentration of the water soluble protein within the amended urine sample in a range of about 1 to 225 mg/mL.

In some aspects, the immunoassay may be selected from the group consisting of a one-step immunoassay, a low wash immunoassay, and a homogenous immunoassay. In some embodiments, the water soluble protein may be recombinant or non-recombinant human serum albumin, porcine serum albumin, castor bean albumin, salmon serum albumin, bovine serum albumin, or a mixture thereof.

In some embodiments, the buffer may be configured to adjust a pH of the urine sample to within a preselected range. The buffer may be selected from the group consisting of: glycine, 3-(N-morpholino)propanesulfonic acid (MOPS), tris(hydroxymethyl)aminomethane (Tris), tricine, acetate, borate, 2-(N-morpholino)ethanesulfonic acid (MES), and 2-[[1,3-dihydroxy-2-(hydroxymethyl)propan-2-yl]amino] ethanesulfonic acid (TES).

In some embodiments, the reagents may further comprise a scavenger configured to reduce non-specific current generation from electroactive species. The scavenger may be a vitamin B scavenger.

In some embodiments, the device may further comprise a component configured to dilute the urine sample with a diluent. The diluted urine sample may comprise about 10% diluent.

In some aspects, the target analyte may be NGAL. In some additional or alternative embodiments, the target analyte may be selected from the group consisting of human chorionic gonadotrophin, troponin I, troponin T, *Chlamydia*, *Legionella*, acetaminophen, amphetamines, methamphetamines, barbiturates, benzodiazepines, cocaine, methadone, opiates, phencyclidine, marijuana, and tricyclic antidepressants.

In some embodiments, the reagents may further comprise urease configured to reduce a urea concentration of the urine sample below a preselected urea threshold. In additional embodiments, the reagents may further comprise glutamine synthetase or any other urea cycle enzyme configured to consume ammonium. In additional embodiments, the reagents may further comprise a sequestering enzyme configured to reduce and sequester excess phosphate below a preselected phosphate threshold.

In yet another embodiment, the present invention is directed to a method for performing an immunoassay for a target analyte in a urine sample. The method comprises providing a test device with reagents disposed in a first region of the test device and at least one electrode disposed in a second region of the test device. The reagents comprise a water soluble protein and a buffer. The method further comprises amending a urine sample with the reagents such that a dissolved concentration of the water soluble protein within the amended urine sample is in a range of about 1 to 225 mg/mL. The method further comprises determining a concentration of the target analyte within the amended urine sample using the at least one electrode.

BRIEF DESCRIPTION OF THE DRAWINGS

The present invention will be better understood in view of the following non-limiting figures, in which:

FIGS. 9A-9E show top, bottom, side, and perspective views of an immunosensor cartridge in a closed position in accordance with some aspects of the invention;

DETAILED DESCRIPTION OF THE INVENTION

Introduction

Figure 1:
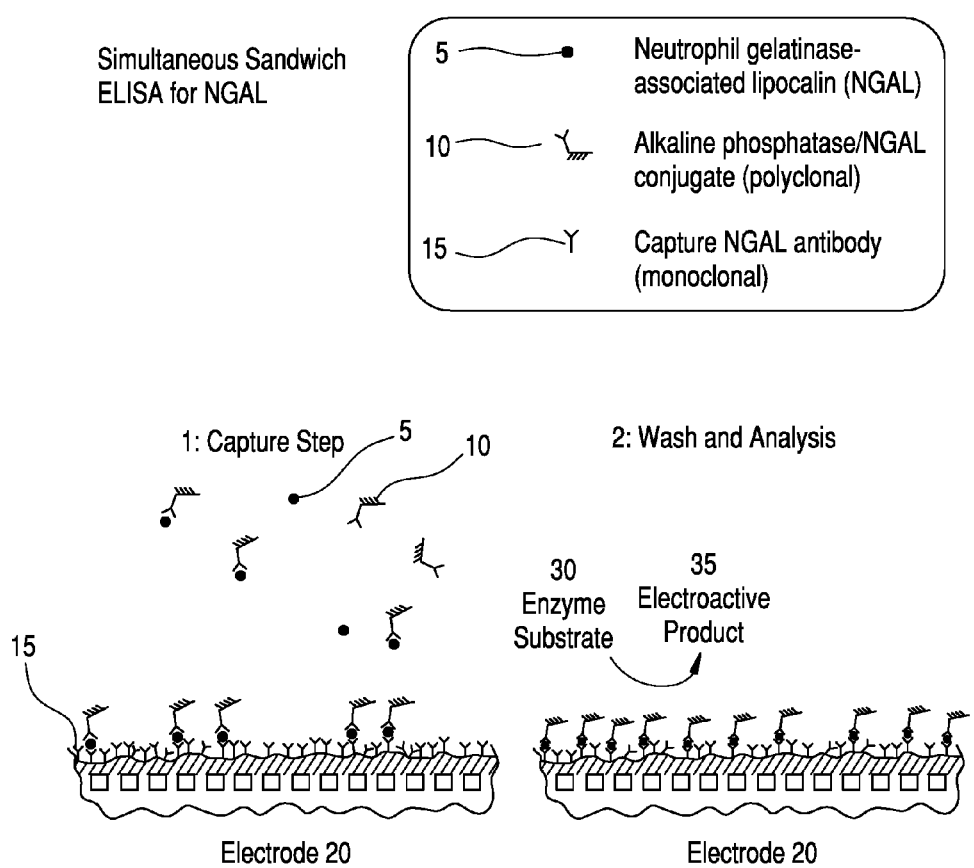
FIG. 1 illustrates the principle of operation of an immunosensor in accordance with some aspects of the invention.

The present invention relates to analytical testing devices and methods for performing electrochemical immunoassays. More specifically, the invention relates to analytical testing devices and methods for performing electrochemical immunoassays on urine samples, and in particular using point of care immunoassays for testing for analytes in urine samples. Some embodiments of the present invention may be implemented by treating or amending a substantially undiluted or diluted urine sample with a reagent comprising urease and/or other enzymes, a water soluble protein, a buffer, scavengers, or combinations thereof to adjust a pH of the amended urine sample to within a preselected range for an immunoassay binding reaction, and performing a quantitative immunoassay on the amended urine sample. The immunoassay may be a one-step immunoassay, a low wash immunoassay, or a homogenous immunoassay.

Some aspects of the present invention are configured for rapid in situ determinations of analytes using a cartridge, preferably a disposable cartridge, having an array of sensors (e.g., a pair of immunosensors comprising a primary sensor and optionally a reference sensor) and a means for sequentially or substantially sequentially presenting a sample (e.g., an amended urine sample) to the sensor array. The cartridges may be configured to be preferably operated with a reading device, such as the reading devices disclosed in U.S. Pat. No. 5,096,669, U.S. Pat. Nos. 5,821,399, and 7,419,821, which are incorporated herein by reference in their entireties. Details of the cartridge and reader device utilized in accordance with these aspects of the present invention are described below in further detail and may be best understood with reference to the commercially available i-STAT® system for performing many different assays including immunoassays.

One embodiment, therefore, of the present invention is directed to a device configured to perform an immunoassay for a target analyte in a urine sample. The device may include a first region (e.g., a first conduit or a first portion of a conduit) that comprises reagents, which are configured to amend the urine sample. The reagents may comprise a water soluble protein and a buffer. The device may further include a second region (e.g., a second conduit or a second portion of a conduit) comprising at least one immunosensor or electrode configured to determine a concentration of the target analyte in the amended urine sample. The first region may be configured to provide a predetermined dissolved concentration of the water soluble protein to the urine sample to form an amended urine sample. The predetermined dissolved concentration of the water soluble protein may be in a range of about 0.02 to 225 mg/mL, e.g., from 0.02 to 200 or from 1 to 100.

In another aspect, the reagents may comprise urease and a buffer. The first region may be configured to provide a predetermined dissolved enzymatic activity within the amended urine sample. The predetermined dissolved urease enzymatic activity may be in a range of about 10 to 10,0000 IU/mL, e.g., from 50 to 5000 or from 100 to 2000.

In another embodiment, the present invention is directed to a device for performing a quantitative immunoassay for a target analyte in a urine sample. As used herein, the term "urine sample" refers to either a diluted or undiluted urine sample. The device may comprise a housing with a first region for receiving a urine sample and amending the urine sample with a dissolvable reagent. The dissolvable reagent, preferably urease combined with albumin and a buffer, may be coated onto a wall of the first region or added beforehand to the urine sample. The device also may have a second region connected to the first region, wherein the second region is configured to receive the amended urine sample and form an immobilized complex between the target analyte, an immobilized first antibody, and an enzyme-labeled second antibody or an enzyme-labeled target analyte molecule.

In operation, therefore, one goal of the present invention is to provide a device such as an immunosensor cartridge that is preferably operated as follows. An unmetered amount of a biological sample (e.g., a urine sample) is placed into a sample chamber of the cartridge, and the cartridge is placed into a reading device. A metered portion of the sample is amended with a reagent comprising urease and/or other enzymes, a water soluble protein, a buffer, scavengers, or a combination thereof, and is then contacted with the at least one immunosensor or electrode. An electrical response of the at least one immunosensor or electrode is recorded and analyzed for the presence, or amount of, an analyte of interest in the amended sample.

Amending Reagent

The general concept for treating or amending the urine sample in the present invention is based on the use of an amending reagent comprising urease and/or another enzyme, a water soluble protein, a buffer, scavengers, or combinations thereof that are provided as a urine-soluble solid matrix, e.g., in a dried printed spot containing various excipients, such as sugars, to stabilize the dried reagent within a conduit of a device (e.g., a cartridge). For example, the reagent may be disposed in a solubilizing agent, e.g., a sugar matrix, within a conduit in the device downstream of where the urine sample is introduced into the device, but upstream of the at least one immunosensor or electrode such that when the urine sample contacts the solubilizing agent, the reagent is solubilized into the urine sample prior to performance of the immunoassay at the at least one immunosensor or electrode.

In some embodiments, the enzyme(s) (e.g., urease) may be added to the reagent to counteract the potential damaging influence of the urine sample on the performance of the immunoassay. Urea is a common component of urine and is known to be a strong protein denaturant that may potentially cause the inactivation of enzymes by unfolding the protein constituting the enzyme into a non-functioning structure. Immunoassays typically use an enzyme (e.g., alkaline phosphatase (ALP), horseradish peroxidase (HRP), and/or glucose oxidase (GOX)) conjugated to a highly specific binding species, such as, an antibody or aptamers for detection of the desired analyte. The enzymes in these conjugates may be susceptible to the denaturing effects of urea present in urine sample. Accordingly, some aspects of the present invention include adding enzymes (e.g., urease) to the urine sample such that the urea concentration in the urine sample may be set and/or maintained below a preselected threshold value, which reduces the potential for interference with detection enzyme (e.g., ALP) activity.

For example, single step immunoassays (e.g., ELISA) that may be used in the present invention generally have both the capture antibody and the detection antibody conjugate present in the same sample. Therefore, when the urine sample contains a denaturing agent, such as urea, the antibody conjugate can lose enzyme activity, potentially providing a false negative or an analytical result that is less than the accurate value. On the other hand, two-step immunoassays function by a first step where the antigen present in a sample first binds to a capture antibody. The sample and unbound antigen are then washed away from the capture antibody. For a urine sample containing high concentrations of urea, the urea is also washed away from the assay. A detection conjugate (which may comprise an enzyme) is then added to the assay, which will not be exposed to urea present in the urine sample. Thus, two-step immunoassays are impacted less by the presence of urea in the urine, as it is washed away in the process.

Moreover, thin layer chromatography assays (TLC) use a solvent that dilutes the original sample, which may reduce the concentration of the urea present in a urine sample at the capture site of the TLC assay, along with the ability of the adsorbing material to bind the urea. Thus, TLC assays may be impacted less by the presence of urea in the urine, as the urea is diluted in the process. Consequently, a one-step immunoassay, a low wash immunoassay, or a homogenous immunoassay may advantageously benefit from the removal of urea in a urine sample. In accordance with some aspects of the invention, immunoassay performance is improved be removing or reducing the urea concentration.

More specifically, in one aspect of the invention, enzymes may be provided to remove or reduce the urea concentration in the urine sample below a preselected threshold value such that the denaturing of proteins used in the immunoassay may be avoided. One degradative enzyme of urea is urease [EC 3.5.1.5], which catalyzes the hydrolysis of urea with water into carbon dioxide and ammonia. Urease functions best when mercaptans like dithiothreitol (DTT) are present in the solution (Perlzweig, 1932, Science, vol 76:435-6). Therefore, mercaptans may also be a component of the reagent. In solution, urease, mercaptans, and ALP are compatible. However, mercaptans can poison a reference electrode (e.g., a Ag/AgCl reference electrode) in an electrochemical immunosensor. Therefore, in some embodiments, urease may be provided with the lowest possible mercaptan concentrations possible as should be understood by those of ordinary skill in the art such that the mercaptans do not interfere with the reference sensor. This may be accomplished by dialyzing or column buffer exchanging the enzyme preparation.

It can be generalized that 1 IU of urease converts about 1 µMol of urea per minute. A 3 µL sample of urine may contain about 0.4 M urea, which would contain approximately 12 µMol of urea. Thus, an excess of urease may be required to convert urea efficiently in less than a minute (e.g., in test systems such as the present invention in which time is a predominant factor). Accordingly, in some embodiments, about 45-55 IU of urease (preferably about 50 IU of urease) may be added to the reagent to provide a dissolved urease enzymatic working range of about 10-10,000 IU/mL.

In some embodiments, the urease may be provided to reduce the urea concentration of the urine sample below a preselected urea threshold, e.g., a preselected threshold of 10 mM. More preferably, the urease may be provided to remove or reduce the urea concentration of the urine sample below the preselected urea threshold of 0.1 mM. Urease catalyzes the following reaction:

In addition to enzymes that remove or reduce the urea concentration (e.g., urease), other enzymes may also be added to the reagent. For example, Metz et al., 1970, *Clinica Chimica Acta*, speculates that an increase in ammonia in a sample when urea is present in an ALP assay may be inhibitory for enzyme activity. Therefore, to overcome this potential problem, another enzyme(s) may be added in some embodiments of the present invention to remove the ammonia, e.g., as it is formed via the urease equilibrium reaction. One potential enzyme for this purpose is glutamic dehydrogenase [EC 1.4.1.2]. Other enzymes that consume ammonia and generate less toxic substrates could also be used for this purpose (e.g., glutamine synthetase [EC 6.3.1.2] or any other urea cycle enzyme configured to consume ammonia). The reaction for glutamic dehydrogenase is as follows:

To assist glutamic dehydrogenase in converting $NH_3$ to L-glutamate, 2-oxoglutarate and NADH may also be added to the reagent such that they are provided in the reaction in excess to assist glutamic dehydrogenase in converting $NH_3$ to L-glutamate.

Furthermore, it should be noted that the use of glutamic dehydrogenase, glutamine synthetase, or other enzymes found in the urea cycle may increase a concentration of phosphate within the sample, which may further inhibit enzyme (e.g., ALP) activity. Thus, it may be advantageous to add an enzyme to the reagent that could sequester and/or reduce the concentration of excess phosphate in the sample. An example of such an enzyme would be adenylate kinase, which is used to regenerate adenosine triphosphate (ATP) from the adenosine diphosphate (ADP) and phosphate created by the action of enzymes such as glutamine synthetase. Accordingly, in some embodiments, the reagent may further comprise a sequestering enzyme configured to sequester and reduce the concentration of phosphate below a preselected phosphate threshold. Preferably, the preselected phosphate threshold may be from 0 to 1 mM, or about $\frac{1}{100}$ the number of enzyme (e.g., ALP) molecules.

Another approach to improve immunoassay performance (e.g., the one-step immunoassay) may be to have an enzyme conjugate that is resistant to denaturing from the presence of urea in the urine sample. For example, neutrophil alkaline phosphatase (NALP) is resistant to urea (Cuckle et al., 1990, BMJ, 301:1024; Denier et al., 2002, BMC Biochemistry, 3(2):1) and may be used for the enzyme conjugate in place of the traditional ALP. Therefore, the use of a urea-resistant enzyme (e.g., NALP) in the immunoassay system of the present invention may alleviate the inhibition of the signal due to the denaturing effect of urea on the enzyme conjugate.

In some embodiments, a water soluble protein may be provided to substantially block non-specific binding of immunoglobulins at the sensor array and throughout conduits of the device. Additionally, the water soluble protein may be provided to increase the viscosity of the urine sample and advantageously improve fluidic control within the device (e.g., improved control of movement of the urine sample from an entry port to a sensor array). In accordance with these aspects of the invention, the water soluble protein may comprise forms of albumin and derivates thereof, forms of casein and derivatives thereof, or forms of whey proteins and derivatives thereof. In the instance of albumin, forms such as, recombinant or non-recombinant human serum albumin, porcine serum albumin, castor bean albumin, salmon serum albumin, bovine serum albumin, or a mixture thereof may be applicable to the aspects of the present invention. Albumin is a water soluble protein coagulated by heat, found in egg white, blood plasma and milk. Plants may also form a source of water soluble albumin proteins. Youle and Huang, (1978, Plant Physiol., 61: 13) also indicate that there are high concentrations of albumins in many seeds. In particular, Youle and Huang found that a specific albumin, 2S, constitutes 40% of the total castor seed protein. Serum Albumin is the predominant plasma protein in Atlantic Salmon (Salmo salar) (Xu & Ding, 2005, Biochemistry and Biotechnology, 35:283). The different forms of albumin can function as a chelator and bind some interferents. Further, it is possible that the albumin can coat the immunosensor to protect it from interferents.

In some embodiments, a buffer may be provided to adjust a pH of the urine sample to within a preselected range for the immunoassay binding reaction. Specifically, it is known that the pH of urine samples may vary widely. However, the urine sample is generally weakly buffered. Therefore, a buffer material may be added to the reagent to re-buffer the urine into a desirable preselected range for the immunoassay binding reaction. Preferably, a buffer may be selected that yields a pH in a preselected range of about pH 6 to pH 10.5. More preferably, a buffer may be selected that yields a pH in a preselected range of about pH 8.5 to pH 9. In some aspects of the present invention, the buffer selected may be glycine, 3-(N-morpholino)propanesulfonic acid (MOPS), tris(hydroxymethyl)aminomethane (Tris), tricine, acetate, borate, 2-(N-morpholino)ethanesulfonic acid (MES), 2-[[1,3-dihydroxy-2-(hydroxymethyl)propan-2-yl]amino]ethanesulfonic acid (TES), or combinations thereof.

In some embodiments, scavengers may be provided to reduce non-specific current generation derived from electroactive species. More specifically, the scavengers may comprise vitamin B scavengers to reduce non-specific current generation derived from electroactive vitamin B species.

Amperometric Electrochemical System for the Detection of a Target Analyte

FIG. 1 illustrates the principle of an amperometric electrochemical system according to specific embodiments of the present invention for determination of a NGAL 5, a marker for AKI. However, it should be understood that while specific embodiments are described for an NGAL assay, the sensor structure and microparticle reagents described herein may also be useful for detecting human chorionic gonadotrophin, troponin I, troponin T, *Chlamydia, Legionella*, acetaminophen, amphetamines, methamphetamines, barbiturates, benzodiazepines, cocaine, methadone, opiates, phencyclidine, marijuana, tricyclic antidepressants, among other analytes.

In a capture step, a sample, e.g., urine, may be introduced into a conduit or sample holding chamber of a cartridge of the present invention (e.g., a cartridge as disclosed in U.S. Pat. No. 7,723,099, which is incorporated herein by reference in its entirety) with a fluidics format suitable for an immunoassay. In some embodiments, the urine sample is substantially undiluted. However, in additional or alternative embodiments, the urine sample may be diluted. For example, a component of the cartridge (as discussed in further detail herein) may be configured to dilute the urine sample with a diluent. In some aspects of the invention, the diluted urine sample may comprise from 5 to 95, from 10 to 90, or about 99% diluent.

In use, the enzymes may be provided in one or more layers, preferably disposed within one or more conduits of the immunoassay device, e.g., cartridge. For example, a first layer may be formed on a portion of a wall of the conduit or the sample holding chamber of the cartridge. The first layer may comprise the amending reagent (a discussed herein comprising urease and/or one or more other enzymes, a water soluble protein, a buffer, scavengers, or a combination thereof), which is configured to amend the urine sample. In addition, a second layer may be provided and formed on a portion (a same or different portion as the portion having the reagent) of a wall of a conduit (a same or different conduit as the conduit having the reagent) comprising a conjugate molecule 10 labeled with an enzyme (e.g., ALP covalently attached to a polyclonal anti-NGAL (e.g., a signal antibody)), which is configured to bind to a target analyte (e.g., NGAL) within the urine sample. For example, the urine sample may be mixed with the amending reagent and the conjugate reagent, which are bound to a surface of the conduit or the sample holding chamber of the cartridge.

The conjugate molecule 10 may specifically bind to the NGAL 5, in the urine sample, producing a complex or conjugate comprising the NGAL 5 bound to an ALP signal antibody 10. In a capture step, the complex comprising the NGAL 5 bound to the ALP may bind to a capture NGAL antibody 15 (e.g., an immobilized antibody) attached on, or close to, at least one amperometric working electrode 20. Accordingly, the at least one amperometric working electrode 20 may be coated with a biolayer comprising the covalently attached capture NGAL antibody 15, to which the complex comprising the NGAL 5 bound to the ALP conjugate molecule 10. The ALP is thus immobilized on or in close proximity to the at least one amperometric working electrode 20.

A capture region on the at least one amperometric working electrode 20 may be defined by a hydrophobic ring of polyimide or another photolithographically produced layer. A microdroplet or several microdroplets (approximately 5-40 nanoliters in size) containing antibodies in some form, for example bound to latex microparticles, may be dispensed on the surface of each sensor. The photodefined ring contains this aqueous droplet allowing the antibody coated region to be localized to a precision of a few microns. The capture region may be made from about 0.03-2 mm$^2$ in size. The upper end of this size (e.g., 2 mm$^2$) may be limited by a size of a sensor conduit comprising the sensors in present embodiments, and is not a limitation of the invention.

In addition to specific binding, the complex comprising the NGAL 5 bound to the ALP signal antibody 10 may also bind non-specifically to the electrode. Non-specific binding may introduce a background signal from the electrode that is undesirable, and preferably should be minimized. Accordingly, in a rinsing step, a rinsing protocol (e.g., a low volume wash or limited wash) that utilizes a segmented fluid to rinse the sensors may provide an efficient means to minimize the background signal. In some embodiments, the limited wash may be less than fifty times a volume of the amended urine sample and/or fewer than three independent cycles of clean wash buffer (e.g., three independent washing steps with fresh wash buffer) as should be understood by those of ordinary skill in the art of immunoassay procedures. In an analysis step subsequent to the rinsing step, a substrate 30 that is hydrolyzed by, for example, ALP to produce a detectable electroactive product 35 may be introduced to the electrode. In specific embodiments, the substrate 30 may be comprised of p-aminophenylphosphate or other suitable material such as a phosphorylated ferrocene.

Thereafter, the ALP attached to the complex reacts with the substrate 30 to form the detectable product 35 that may be indicative to a concentration of the captured NGAL 5 within the urine sample. The detectable product 35 causes an electrical potential to be generated across the at least one amperometric working electrode 20 that in turn generates a signal relative to the electrical potential caused by the detectable product 35. The detectable product 35 generated from the reaction of the ALP with the substrate 30 at the at least one amperometric working electrode 20 may be essentially proportional to an amount of NGAL 5 initially present in the urine sample.

In some embodiments, the substrate 30 may comprise a p-aminophenol species, and may be selected such that a voltammetric half-wave potential ($E_{1/2}$) of the substrate 30 and the detectable electroactive product 35 differ substantially. Preferably, the $E_{1/2}$ of the substrate 30 is substantially higher (more positive) than that of the product 35. For example, when the $E_{1/2}$ of the substrate 30 is substantially higher (more positive) than that of the product 35, the product 35 can be selectively electrochemically measured in the presence of the substrate 30.

The detection of ALP activity in the above example relies on a measurement of the p-aminophenol oxidation current. This is achieved at a potential of about +20 to +60 mV, or from about +25 to +35 mV versus an optional Ag/AgCl ground or reference electrode. The exact form of detection used depends on the sensor configuration. In one embodiment of the sensor, an array of gold microelectrodes may be located directly beneath the antibody capture region (e.g., the biolayer). When the analysis fluid is pulled over the array of gold microelectrodes, enzyme located on the capture site converts the p-aminophenylphosphate to p-aminophenol in an enzyme-limited reaction. The concentration of the p-aminophenylphosphate may be selected to be in excess, e.g., 10 times the Km value. The analysis solution is 0.1 M in diethanolamine, 1.0 M NaCl, buffered to a pH of 9.8. Additionally, the analysis solution may comprise 0.5 mM MgCl, which is a cofactor for the enzyme. Alternatively, a carbonate buffer has the desired properties and may be included in the analysis fluid.

Amperometric Working Electrode Fabrication

Figure 2:
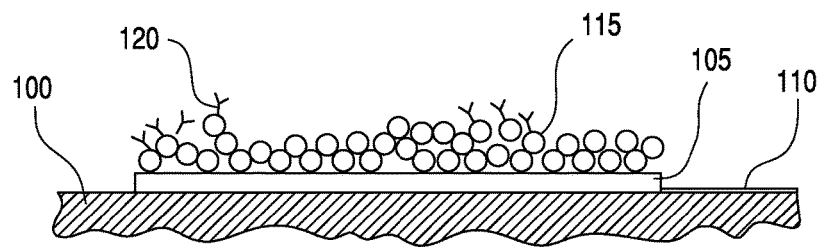
FIG. 2 shows a side view of the fabrication of an immunosensor in accordance with some aspects of the invention.

Preferred embodiments of a microfabricated sensor array comprising at least one amperometric working electrode is shown in FIG. 2. In the preferred embodiments, the microfabricated sensor array may comprise a pair of immunosensors or electrodes comprising a primary sensor or electrode and optionally a reference sensor or electrode. For example, the immunosensors or electrodes may be fabricated as adjacent structures, respectively, on a silicon chip.

In the preferred embodiments, the electrodes may be formed with gold surfaces coated with a photodefined layer of polyimide. For example, wafer-level microfabrication of a preferred embodiment of the sensor array may be achieved as follows. A planar non-conducting substrate 100 may be used as a base for the sensor array. A conducting layer 105 may be deposited on the substrate 100 by conventional means or microfabrication known to those of skill in the art to form at least one electrode. The conducting layer 105 may comprise a noble metal such as gold or platinum, although other unreactive metals such as iridium may also be used, as many non-metallic electrodes of graphite, conductive polymer, or other materials may also be used.

For example, a base electrode may comprise a square array of 5-10 µm gold disks, e.g., 7 µm gold disks, on 15 µm centers. The array may cover a region, e.g., a circular region, approximately 300 to 900 µm in diameter, optionally 600 µm in diameter, and may be formed by photo-patterning a thin layer of the polyimide of thickness 0.35 µm over a substrate made from a series of layers comprising Si, $SiO_2$, TiW, and/or Au, or combinations thereof. The array of microelectrodes affords high collection efficiency of electroactive species with a reduced contribution from any electrochemical background current associated with the capacitance of the exposed metal. In particular, regularly spaced openings in the insulating polyimide layer define a grid of small gold electrodes at which the p-aminophenol may be oxidized in a 2 electron per molecule reaction.

Microfabrication techniques (e.g. photolithography and plasma deposition) may be utilized for construction of the multilayered sensor structures in confined spaces. For example, methods for microfabrication of the electrochemical immunosensors on silicon substrates are disclosed in U.S. Pat. No. 5,200,051, which is hereby incorporated by reference in its entirety. These include dispensing methods, methods for attaching biological reagent, e.g., antibodies, to surfaces including photoformed layers and microparticle latexes, and methods for performing electrochemical assays.

The microfabricated sensor array may also comprise an electrical connection 110 and a biolayer 115 (as discussed above with respect to FIG. 1), which are deposited onto at least a portion of the conducting layer 105 and/or the non-conducting substrate 100. In the present invention, the biolayer 115 may include a porous layer comprising a surface with a sufficient amount of a molecule 120 (e.g., the immobilized antibody and/or the microparticle reagent) that may either bind to an analyte of interest, or respond to the presence of such an analyte by producing a change that is capable of measurement.

Optionally, a permselective screening layer may be interposed between the conducting layer 105 and the biolayer 115 to screen electrochemical interferents as described in U.S. Pat. No. 5,200,051, which is hereby incorporated by reference in its entirety. In particular, the electrodes described herein may be manufactured to optimize a signal-to-noise ratio, or amperometric background signal. For example, an intervening polyvinyl alcohol (PVA) layer of about 0.5-5.0 µm thickness (preferably 0.6-1.0 µm) may be placed between the electrodes and the biolayer or antibody reagent layer significantly attenuating the background component, as described in U.S. Pat. No. 7,723,099, which is hereby incorporated by reference in its entirety. An advantage of PVA as the background-reducing layer is that noise is reduced without appreciably affecting the Faradaic component of the signal. While the PVA layer reduces the diffusion coefficient of small molecules by about 50% it has been found that it does not change the current at the coated electrodes, for two reasons. First, with PVA layers of about 1 micron thickness, the detected electroactive species is present in a diffusion layer of at least ten times that thickness, so there is little decrease in transport due to the PVA layer. Second, a steady-state current is measured in the immunosensor, which is effectively independent of the transport rate and electrode kinetics, but is a function of the enzymatic rate of production of the detectable species, such as p-aminophenol generated from p-aminophenylphosphate by the enzyme ALP (attached to the signal antibody).

The porous PVA layer may be prepared by spin-coating an aqueous mixture of PVA plus a stilbizonium photoactive, cross-linking agent over the microelectrodes on the wafer. The spin-coating mixture optionally includes bovine serum albumin (BSA). The spin-coating mixture may then be photo-patterned to cover only a region above and around the sensor arrays, and preferably has a thickness of about 0.6 µm.

In specific embodiments, the biolayer 115 may be formed from latex beads of specific diameter in the range of about 0.01 to 5.0 µm. The beads may be modified by covalent attachment of any suitable molecule consistent with the above definition of the biolayer (as discussed in further detail below). Many methods of attachment exist in the art, including providing amine reactive N-hydroxysuccinimide ester groups for the facile coupling of lysine or N-terminal amine groups of proteins. In specific embodiments, the molecule is an antibody selected to bind one or more of NGAL, human chorionic gonadotrophin, troponin I, troponin T, *Chlamydia*, *Legionella*, acetaminophen, amphetamines, methamphetamines, barbiturates, benzodiazepines, cocaine, methadone, opiates, phencyclidine, marijuana, tricyclic antidepressants, or modified fragments thereof, more preferably NGAL. Such modified fragments are generated by oxidation, reduction, deletion, addition or modification of at least one amino acid, including chemical modification with a natural moiety or with a synthetic moiety. Preferably, the molecule binds to the analyte specifically and has an affinity constant for binding analyte ligand of about $1\times10^{-7}$ to $1\times10^{-15}$.

In one embodiment, the biolayer 115 comprising microparticle beads having surfaces that are covalently modified by a suitable molecule, may be affixed to the sensors by the following method. A microdispensing needle may be used to deposit onto a surface of the electrode or a photo-patterned PVA permselective layer covering the electrode a small droplet of the microparticle reagents. Specifically, in order to bind the microparticle reagents to the electrode, a droplet of about 0.4 nL comprising about 1% solids (i.e., the microparticles) in 0.08% Tween 20 may be microdispensed (e.g., using the method and apparatus of U.S. Pat. No. 5,554,339, which is incorporated herein by reference in its entirety) onto a surface of the electrode or a photo-patterned PVA permselective layer covering the electrode. The droplet may then be allowed to dry. The adherence of the dried microparticles particles to the porous layer substantially prevents dissolution of the microparticles into the sample (e.g., the urine sample) or the washing fluid. However, in some embodiments additional coupling chemistry may be used to ensure bead immobilization on the porous layer and/or the immunosensors. Such techniques are well known in the art.

Microparticle Reagent Fabrication

In some embodiments, microparticles (e.g., carboxylate-modified latex microparticles supplied by Bangs Laboratories Inc. or Seradyn Microparticles Inc.) coated with antibodies (e.g., anti-NGAL and anti-HSA) may be prepared for use in detecting target analytes such as NGAL in accordance with some aspects of the present invention. For example, the microparticles may first be buffer exchanged by centrifugation, and then the antibodies may be added to the microparticles (e.g., the antibodies may be allowed to passively adsorb onto the microparticles). In active groups (e.g., carboxyl groups) on the microparticles may then be activated to form amide bonds to the antibodies (e.g., anti-NGAL and anti-HSA). Microparticle aggregates may then be removed by centrifugation and the finished microparticles may be stored frozen for future use with the systems and devices of the present invention.

More specifically, NGAL capture/analyte beads may be prepared as follows: 10 mg of 0.2 carboxylated microparticles (10% weight/volume) may be buffer exchanged into 25 mM 2-(N-morpholino)ethanesulfonic acid (MES, pH 6.2). The microparticles may then be reacted with 0.15 mg anti-HSA mAb for 20 minutes at 4° C. with rotation. Subsequently, 0.8 mg of NGAL mAb may be added to the microparticle/anti-HSA mixture and rotated at 4° C. for an additional 20 minutes, then centrifuged to remove the supernatant. After resuspension of the pellet in 25 mM MES buffer (to achieve 2.5% wt microparticles), 6 mM carbodiimide (EDAC) may be added to the sample and reacted for 2 hours at 4° C. This may then be followed by centrifuging the sample and washing the pellet with ⅕ physiological phosphate buffer twice. A formulated sample with 6.4% solids in ⅕ physiological phosphate buffer may then be further diluted with a protein stabilization solution to 3.2% solids. The formulated sample may then be rotated at 4° C. for 20 minutes, aliquoted, and stored at −80° C. for future use.

NGAL reference bead preparation may be as follows: the process may be the same as NGAL capture/analyte beads process except using only 0.8 mg anti-HSA antibody in the reaction. The use of reference beads in immunosensor manufacture and operation is described in U.S. Pat. No. 7,732,099, which is incorporated herein by reference in its entirety, in which an immuno-reference sensor is used to subtract a signal arising from non-specific binding of the signal antibody to the immunosensor.

Signal Antibody Conjugate Fabrication

In some embodiments, conjugates comprising an antibody (e.g., anti-NGAL) labeled with an enzyme may be prepared for use in detecting target analytes such as NGAL in accordance with some aspects of the present invention. Specifically, conjugate synthesis may comprise the following: NGAL conjugate preparation may use 1.4 mg pepsin digested whole antibody to make F(ab)2' in 0.1 M citrate buffer (pH 3.5) at 37° C. for 45 minutes (0.004 mg pepsin to 1 mg whole Ab). The pepsin digest may be stopped by the addition of Trizma base until the pH of the solution is adjusted to 7.2. The sample may then be cooled at 4° C. for 1 hour. Purification of the F(ab)2' fraction may be performed by using a HiPrep 16/60 Sephacryl S-300 High Resolution size exclusion column. Monoethanolamine hydrochloride (MEA) in ⅕ physiological phosphate buffer may be used to reduce F(ab)2' to Fab-SH (final concentration is 6 mg/mL MEA) for 1 hour at 37° C. The Fab-SH may then be reacted with activated single molecule alkaline phosphatase (ALP) in a 3:1 molar ratio at 4° C. overnight. ALP may previously be activated in the presence of LC-SMCC (Succinimidyl-4-[N-Maleimidomethyl]cyclohexane-1-carboxy-[6-amido-caproate] for 40 minutes at room temperature) at a 10 LC-SMCC:1 ALP molar ratio. The Fab-SH/ALP mixture may then be quenched with 50 mM Tris in conjugation buffer at 4° C. for 1 hour. A size exclusion column may then be used to purify the conjugate fraction and formulate it into a ⅕ physiological phosphate-buffered protein stabilization solution. This NGAL conjugate may then be stored at 4° C. for future use.

Competitive ELISA ALP-NGAL Tracer Fabrication

In some embodiments, activation of alkaline and rhNGAL proteins may be carried out prior to final conjugation. To thiolate the alkaline phosphatase, 10 mg of AP in 0.56 mL buffer (5 mM Tris, 50% glycerol, 5 mM $MgCl_2$, 1 mM $ZnCl_2$) may be exchanged into activation buffer (PBS+10 mM EDTA, pH 7.4) using a 10K MWCO Amicon spin tube. The protein may then be suspended in 1 mL final volume of PBS 10 mM EDTA, pH 7.4 and reacted with 35 μL of 2-Iminothiolane (3.5 mg/mL DMSO stock). The solution may then be nutated for 1 hour at room temperature. The reaction may then be washed 3 times and exchanged into 1 mL coupling buffer (PBS pH 7.4) using a 10K MWCO Amicon filter.

Maleimide activation of rhNGAL may be carried out by addition of 16 μL sulfo-SMCC (1 μg/μL stock in DMSO) to 77 μg rhNGAL in PBS pH 7.4 (reaction volume 316 μL total). The reaction may be nutated for 2 hours at room temperature. The reaction may then be washed 3 times and exchanged into 200 μL coupling buffer (PBS pH 7.4) using a 10K MWCO Amicon filter.

Final conjugation of activated AP to activated rhNGAL may be carried out by adding 26 μL activated AP from above into a 200 μL activated rhNGAL vial. The reaction may be nutated at room temperature for 1 hour and then allowed to proceed to completion at 4° C. overnight. The rhNGAL-AP conjugate (NGAL tracer) may then be washed 3 times with TBS, pH 8 using an Amicon 100K MWCO filter tube which enabled removal of unreacted rhNGAL (~25000 kDa). The NGAL tracer may then be suspended in 231 μL 1% BSA in TBS. Any dilutions of the tracer used for off-cartridge immunoassay may then be made in 1% BSA in TBS, while dilutions for on-cartridge assays may be made directly in donor urine.

System Comprising a Sensor Array Configured for Target Analyte Detection

Figure 3:
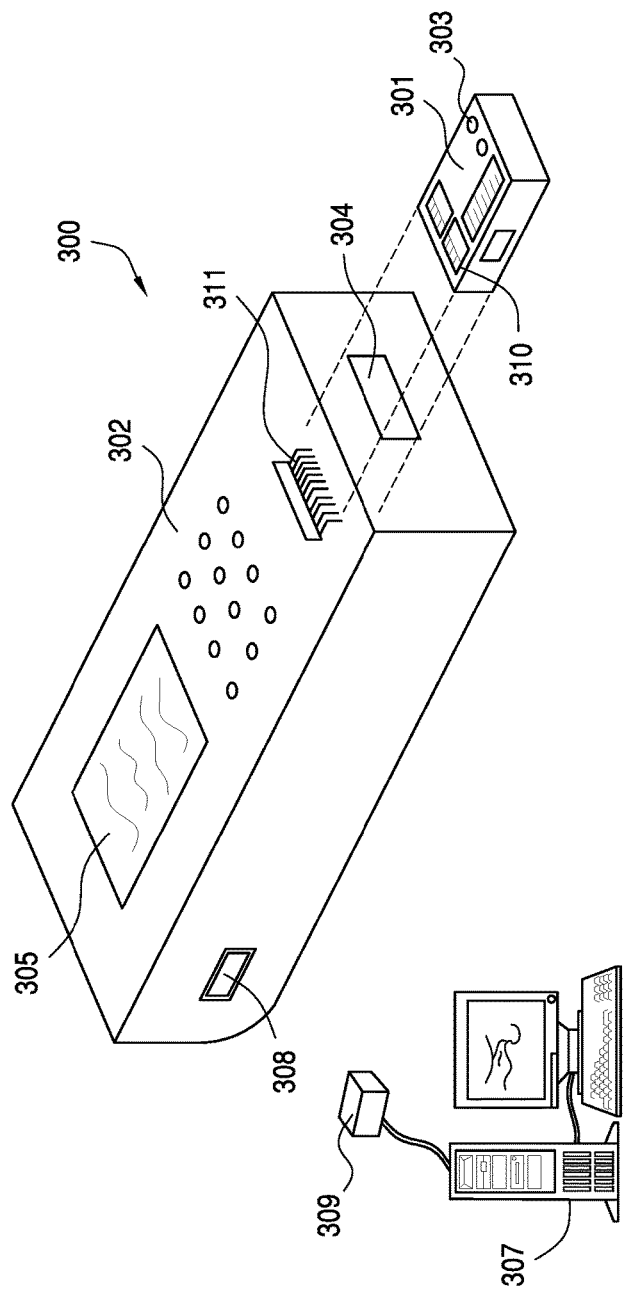
FIG. 3 shows an isometric view of a disposable sensing device and reader device in accordance with some aspects of the invention.

Referring to FIG. 3, the system 300 of the present invention may comprise a self-contained disposable sensing device or cartridge 301 and a reader device or instrument 302. A fluid sample (e.g., urine) to be measured is drawn into a sample entry orifice or port 303 in the cartridge 301, and the cartridge 301 may be inserted into the reader device 302 through a slotted opening 304. The reader device 302 may comprise a processor configured to perform measurements of analyte concentration within the fluid sample, as discussed herein in further detail. Measurements and determinations performed by the reader may be output to a display 305 or other output device, such as a printer or data management system 307 via a port on the reader 308 to a computer port 309. Transmission can be via Wifi, Bluetooth link, infrared and the like. Note that where the sensors are based on electrochemical principles of operation, the sensors 310 (e.g., a primary sensor and optionally a reference sensor) in the cartridge 301 make electrical contact with the instrument 302 via an electrical connector 311. For example, the connector may be of the design disclosed in jointly owned U.S. Pat. No. 4,954,087, incorporated herein by reference in its entirety. The instrument 302 may also include a method for automatic fluid flow compensation in the cartridge 301, as disclosed in jointly owned U.S. Pat. No. 5,821,399, which also is incorporated herein by reference in its entirety.

In some aspects of the invention, the cartridge 301 may be provided with a barcode with factory set information including equations to be used and required test coefficients. The reader device 302, into which the cartridge 301 is inserted to run the test, may thus be equipped with a barcode reader. A selection of equations may be embedded in software of the reader device 302. For example, the coefficients for the cartridge 301 may differ, where different lots of cartridges 301 are manufactured, each lot having slightly different factory-determined characteristics. In any event, the coefficients for the cartridge 301, from whichever manufacturing lot the cartridge 301 is drawn, are conveyed to the reader device 302 for use in one or more of the equations, for that particular cartridge test. For example, if a given digit of the cartridge barcode is set to 1, the reader device 302 may set a predetermined coefficient to zero, whereas other digits may code for different coefficients or select a kinetic model to be used, e.g., an immunoassay model formulated by analogy to the well-known Michaelis-Menton enzyme kinetics.

Figure 4:
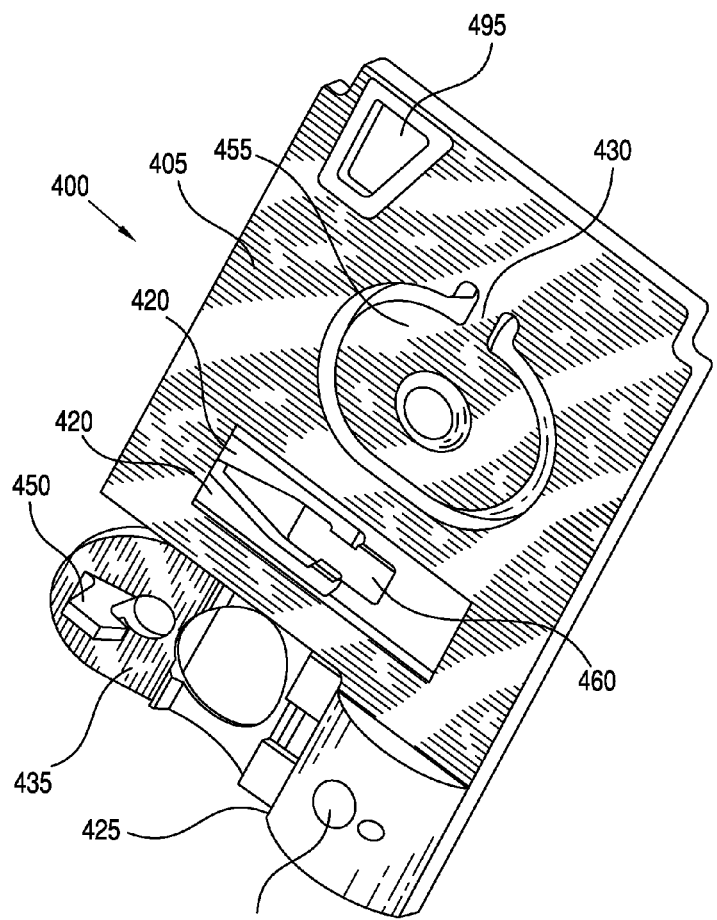
FIG. 4 shows an isometric top view of an immunosensor cartridge cover in accordance with some aspects of the invention.
Figure 5:
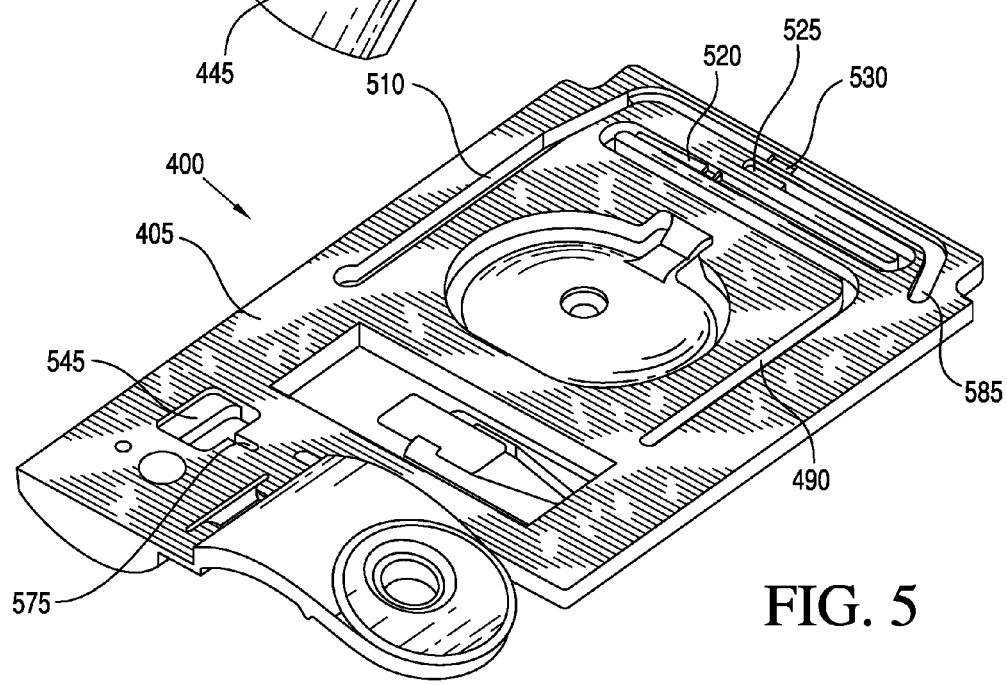
FIG. 5 shows an isometric bottom view of an immunosensor cartridge cover in accordance with some aspects of the invention.
Figure 6:
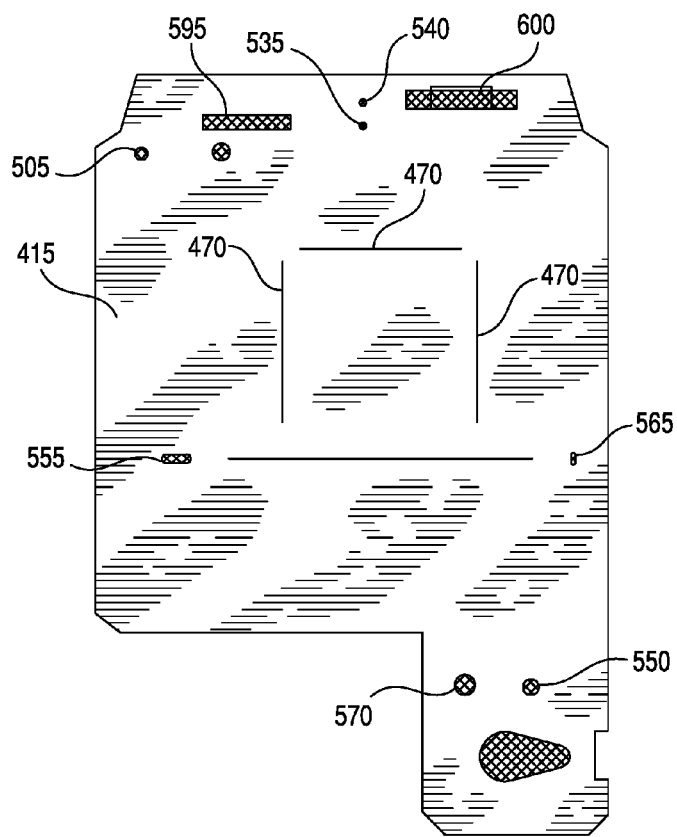
FIG. 6 shows a top view of a tape gasket in accordance with some aspects of the invention.
Figure 7:
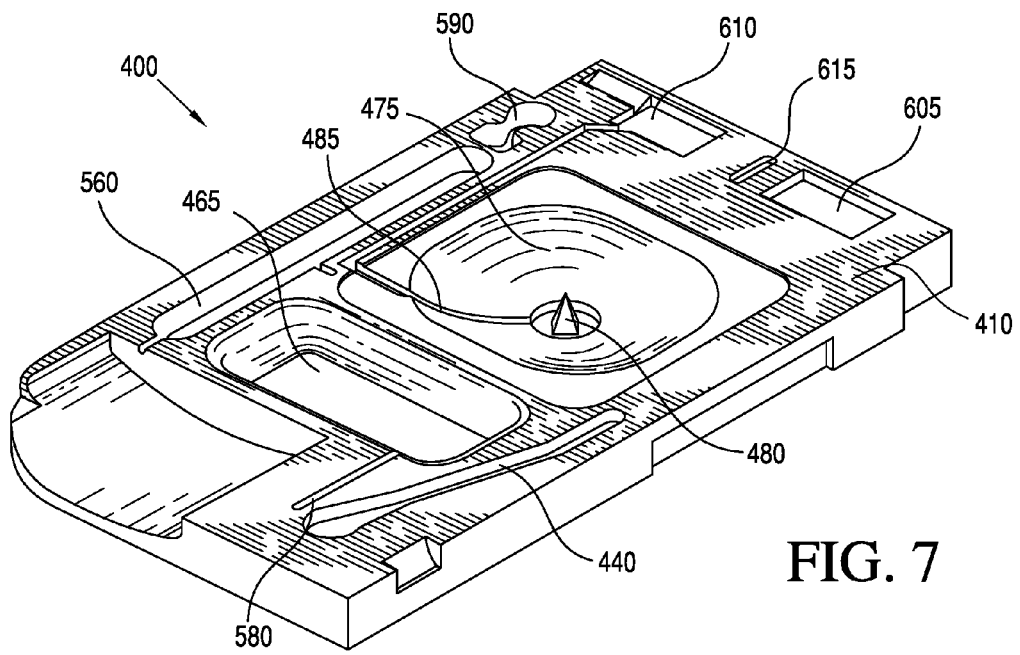
FIG. 7 shows an isometric top view of an immunosensor cartridge base in accordance with some aspects of the invention.

In one embodiment, as shown in FIGS. 4-7, a cartridge 400 (e.g., a disposable assay cartridge) may comprise a cover 405 (as shown in FIGS. 4 and 5), a base 410 (as shown in FIG. 7), and a thin-film adhesive gasket 415 (as shown in FIG. 6) that is disposed between the base 410 and the cover 405. The cartridge 400 may be configured for insertion into a reader device, and therefore the cartridge 400 may comprise a plurality of mechanical and electrical connections (not shown) for this purpose. Advantageously, a feature of the cartridge 400 is that once a sample is loaded within the cartridge 400, analysis of the sample may be completed and the cartridge 400 may discarded without an operator or others contacting the sample.

Referring to FIG. 4, the cover 405 may be made of a rigid material, preferably plastic, and capable of repetitive deformation at flexible hinge regions 420, 425, and 430 without cracking. The cover 405 may comprise a lid 435, attached to a main body of the cover 405 by the flexible hinge 425. In operation, after introduction of a sample into a sample holding chamber 440 (as shown in FIG. 7) through a sample entry port 445, the lid 435 may be secured over an entrance to the sample entry port 445, preventing sample leakage. The lid 435 may be held in place by a hook 450.

The cartridge 400 optionally may also have a closure feature as described in jointly owned U.S. Pat. No. 7,682,833, which is hereby incorporated by reference in its entirety, for sealing the sample entry port 445 in an air-tight manner. This closure device may be slidable with respect to a body of the cartridge 400 and provides a shearing action that displaces excess sample located in the region of the sample entry port 445, reliably sealing a portion of the sample in the sample holding chamber 440 between the sample entry port 445 and a capillary stop. Specifically, the cartridge 400 may be sealed by slidably moving a sealing element over the surface of the cartridge in a manner that displaces excess fluid sample away from the sample entry port 445, seals a volume of the fluid sample within the internal fluid sample holding chamber 440, and inhibits fluid sample from prematurely breaking through the internal capillary stop.

The cover 405 may further comprise two paddles 455 and 460 that are moveable relative to the body of the cover 405, and which are attached to the cover 405 by the flexible hinge regions 420 and 430. The paddle 460 may be configured to be operated by a pumping means such that a force is exerted upon an air bladder comprised of cavity 465 (as shown in FIG. 7) and the gasket 415. Operation of the paddle 460 displaces fluid within conduits of the cartridge 400.

The paddle 455 may be configured to be operated upon by a second pumping means such that a force is exerted upon the gasket 415, which can deform because of slits 470 cut therein (as shown in FIG. 6). Deformation of the gasket 415 may transmit pressure onto a fluid-containing foil pack filled with a fluid, e.g., approximately 130 μL of analysis/wash solution or fluid, located in cavity 475 (as shown in FIG. 7), rupturing the foil pack upon spike 480, and expelling fluid into conduit 485. The conduit 485 may be connected via a short transecting conduit in the base 410 to a conduit 490 (as shown in FIG. 5). The fluid fills a front of the conduit 485 first pushing fluid into a small opening in the gasket 415 that acts as a capillary stop.

Additional action in the cartridge 400 generated by mechanisms within the reading device applied to the cartridge 400 may be used to inject one or more air segments into the fluid at controlled positions within the conduit 490. The air segments may be used to wash a sensor surface of the sensor array and the surrounding conduit 490 with a minimum amount of fluid (e.g., a limited wash cycle in which the volume of wash may be less than fifty times a volume of the amended urine sample and/or fewer than three independent cycles of clean wash buffer (e.g., three independent washing steps with fresh wash buffer) as should be understood by those of ordinary skill in the art of immunoassay procedures. For example, the cover 405 may further comprise a hole covered by a thin pliable film 495. In operation, pressure exerted upon the film 495 may expel one or more air segments into the conduit 490 through a small hole 505 in the gasket 415 (as shown in FIGS. 5 and 6).

Referring to FIG. 6, a lower surface of the cover 405 further comprises the conduit 490 and another conduit 510. The conduit 490 includes a constriction 520 that controls fluid flow by providing resistance to the flow of the fluid. Optional coatings 525 and 530, e.g., dry reagent coatings, may provide hydrophobic surfaces on the conduit 510, which together with gasket holes 535 and 540 control fluid flow between conduits 190 and 510. A recess 545 in the base may provide a pathway for air to enter and/or escape the conduit 440 through hole 550 in the gasket.

Referring to FIG. 6, the thin-film gasket 415 comprises various holes and slits to facilitate transfer of fluid and air between conduits within the base 405 and the cover 410, and to allow the gasket 415 to deform under pressure where necessary. Specifically, a hole 555 may permit fluid to flow from the conduit 490 into a waste chamber 560, a hole 565 may comprise a capillary stop between conduits 440 and 510, a hole 570 may permit air to flow between a recess 575 (as shown in FIG. 5) and a conduit 580 (as shown in FIG. 7), the hole 550 provides for air movement between the recess 545 and the conduit 440, and the hole 505 permits fluid to flow from a conduit 585 (as shown in FIG. 5) to the waste chamber 560 via optional closeable valve 590 (as shown in FIG. 7). Holes 595 and 600 permit a plurality of electrodes (e.g., the primary sensor and optionally the reference sensor) that are housed within cutaways 605 and 610, respectively, to contact fluid within the conduit 490. In a specific embodiment, cutaway 610 houses a ground electrode, and/or a counter-reference electrode, and cutaway 605 houses at least one analyte sensor (e.g., the primary sensor), and optionally, a reference sensor.

Referring to FIG. 7, the conduit 440 may be configured as a sample holding chamber that connects the sample entry port 445 to the conduit 510 in the assembled cartridge 400. The cutaway 605 may house at least one analyte sensor (e.g., the pair of electrodes), or an analyte responsive surface, together with an optional conductimetric sensor or sensors. The cutaway 610 may house a ground electrode if needed as a return current path for an electrochemical sensor, and may also house an optional conductimetric sensor. A cutaway 615 may provide a fluid path between gasket holes 535 and 540 such that fluid may pass between the conduits 490 and 510. Recess 475 houses a fluid-containing package, e.g., a rupturable pouch, in the assembled cartridge 400 that may be pierced by the spike 480 because of pressure exerted upon paddle 455 upon insertion of the cartridge 400 into the reading device. Fluid from the pierced package flows into the conduit 485. The air bladder may be comprised of the recess 465, which is sealed on its upper surface by the gasket 415. The air bladder may be one embodiment of a pump means, and may be actuated by pressure applied to the paddle 460, which displaces air in the conduit 580 and thereby displaces the sample from the sample chamber 440 into the conduit 510.

In some embodiments, a metering means may optionally comprise the sample chamber 440 bounded by the capillary stop 565 and having along the chamber 440 length an air entry point (gasket hole 550) from the bladder. Air pressure exerted at the gasket hole 550 drives a metered volume of the sample past the capillary stop 565. Therefore, a metered volume of sample may be predetermined by a volume of the sample chamber 440 between the air entry point 550 and the capillary stop 565. An amount of the sample corresponding to this volume may be displaced into the conduit 510 when the paddle 460 is displaced. This arrangement may therefore provide a metering means for delivering a metered amount of an unmetered sample into the various downstream conduits of the cartridge 400. The metering may be advantageous in some embodiments if quantitation of the analyte is required. Thus, an operator may be relieved of accurately measuring the volume of the sample prior to measurement saving time, effort, and increasing the accuracy and reproducibility.

Figure 8:
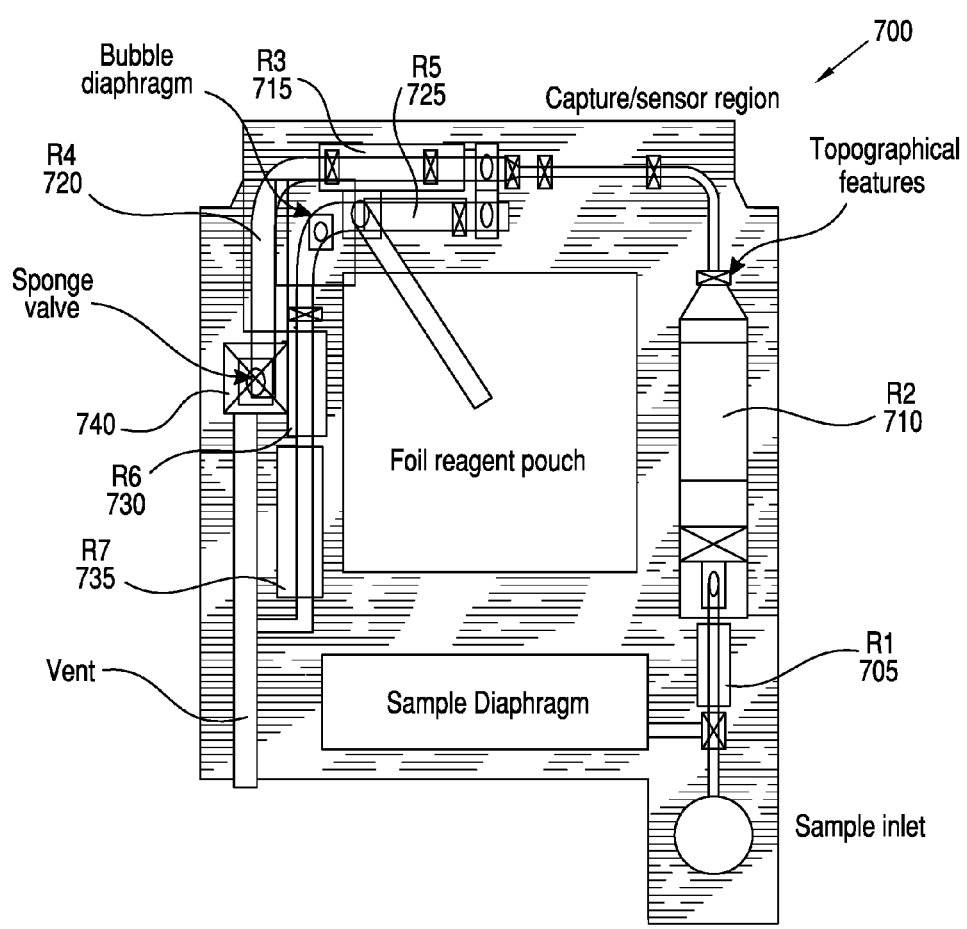
FIG. 8 shows a schematic view of the layout of an immunosensor cartridge in accordance with some aspects of the invention.

As shown in FIG. 8, a schematic diagram of the features of the cartridge 700 and components therein is provided. Specifically, in preferred embodiments, the conduits and the sample chamber 705-735 may be coated with dry reagents to amend the sample or fluid as discussed herein. The sample or fluid may be passed at least once over the dry reagent to dissolve the dry reagent. Reagents that may be used to amend samples or fluid within the cartridge include urease and/or other enzymes, a water soluble protein, a buffer, scavengers, or combinations thereof, antibody-enzyme conjugates, and/or blocking agents that prevent either specific or non-specific binding reactions among assay compounds. A surface coating that may not be soluble but helps prevent non-specific adsorption of assay components to the inner surfaces of the cartridge 700 may also be provided.

For example, within a segment of the sample or fluid, an amending substance may be preferentially dissolved and concentrated within a predetermined region of the segment. In one embodiment, this may be achieved through control of the position and movement of the segment within the conduits and the sample chamber 705-735. Therefore, if only a portion of a segment, such as the leading edge, is reciprocated over the amended substance, then a high local concentration of the substance can be achieved close to the leading edge. Alternatively, if a homogenous distribution of the substance is desired, for example if a known concentration of an amending substance is required for a quantitative analysis, then further reciprocation of the sample or fluid may result in mixing and an even distribution.

In preferred embodiments, a closeable valve 740 may be provided between a first conduit and the waste chamber. In one embodiment, the valve 740 may be comprised of a dried sponge material that is coated with an impermeable substance. In operation, contacting the sponge material with the sample or a fluid may result in swelling of the sponge to fill the cavity (e.g., the valve 590 cavity as shown in FIG. 7), thereby substantially blocking further flow of liquid into the waste chamber. Furthermore, the wetted valve 740 may also be configured to block the flow of air between the first conduit and the waste chamber, which permits a first pump means connected to the sample chamber to displace fluid within a second conduit, and to displace fluid from the second conduit into the first conduit in the following manner.

After the sample is exposed to the sensor array (e.g., the primary electrode and optionally the reference electrode) for a controlled time, the sample may be moved into a post-analytical conduit where the sample may be amended with another reagent. The sample may then be moved back to the sensor array and a second reaction period may begin. Alternately, the post-analysis conduit may serve simply to separate the sample segment from the sensor array. Within the post-analysis conduit may be a single closeable valve that connects an air vent of the sensor conduit to a diaphragm air pump. When the single closeable valve closes, the sample may be locked in the post analytical conduit and cannot be moved back to the sensor array. Such closable valves are described in U.S. Pat. No. 7,682,833, the entirety of which is incorporated herein by reference. In some embodiments, one or more air segments may be injected into the sample to facilitate washing using an active feature, e.g., a pump, or a passive feature, e.g., a tape gasket, as described in U.S. Pat. No. 8,309,364, the entirety of which is incorporated herein by reference.

In a preferred embodiment of the present invention, the sample and a fluid, e.g., a combined wash and enzyme substrate delivery fluid, may contact the sensor array (e.g., the pair of electrodes and optionally the reference electrode) at different times during an assay sequence. The sample and the fluid may also be independently amended with other reagents or compounds present initially as dry coatings within respective conduits of a test device, e.g., the cartridge. Controlled motion of the fluid by the above-described pumping means within the cartridge further permits more than one substance to be amended into each fluid whenever the sample or the fluid is moved to a new region of the conduit. In this manner, multiple amendments to each fluid may be accommodated, extending the complexity of automated assays that can be performed in the cartridge. Therefore, the utility of the present invention may be enhanced.

In an alternative embodiment, as shown in FIGS. 9A-9E, the cartridge 900 may include a housing that comprises two complimentary halves of a cartridge (e.g., the cover 901 and the base 902), which can be bonded together to abut and attach the two complimentary interior surfaces of the two halves in a closed position. In some embodiments, the cover 901 and the base 902 are injection molded, for example, by machine as disclosed in U.S. patent application Ser. No. 13/530,501, filed on Jun. 22, 2012, which is incorporated herein by reference in its entirety. Preferably, the cover 901 is injection molded where a first substantially rigid zone 920 is formed in a first injection molding step and a substantially flexible zone 922 is formed in an additional injection molding step. Preferably, the base 902 is injection molded where a second substantially rigid zone 924 is formed in a first injection molding step.

As shown in FIGS. 9A-9E, the substantially rigid zones 920 and 924 of the cover 901 and the base 902, respectively, are preferably each a single contiguous zone; however, the molding process can provide a plurality of non-contiguous substantially rigid zones. The substantially flexible zone 922 is preferably a set of several non-contiguous zones. For example, the substantially flexible zone 922 around a displaceable membrane 925 may be separate and distinct from the substantially flexible zone at a closeable sealing member 928. Alternatively, the substantially flexible zone may comprise a single contiguous zone.

In a preferred embodiment, the cartridge housing comprises a sensor recess 930 in a portion of the substantially flexible zone. An advantage is that the sensors 935 (e.g., the primary sensor and optionally the reference sensor preferably each of a size of about 0.3×0.4 cm), which are disposed in the sensor recess 930 preferably are made on a silicon wafer substrate, which is relatively brittle. Thus, providing a substantially flexible sensor recess 930 results in a suitable support that can protect the sensor from cracking during assembly. Note that other non-silicon based sensors may be used, e.g., those made on a plastic substrate; however, the preferred embodiment uses sensors of the type described in U.S. Pat. Nos. 5,200,051; 5,514,253; and 6,030,827, the entireties of which are incorporated herein by reference. In addition to being substantially flexible, sensor recess 930 may be best selected to form a liquid-tight and/or air-tight seal around the sensor perimeter, thereby ensuring that liquids do not leak out of the conduit that covers the sensor in the fully assembled cartridge. In an alternative embodiment, sensor recess 930 can be formed in a portion of the substantially rigid zone (as shown in FIG. 7) of either or both of the cover or the bottom of the housing. In this aspect, a liquid-tight and/or air-tight seal optionally may be formed by the double-sided adhesive sheet 415 or gasket (as shown in FIG. 6).

With regard to overall dimensions, the preferred embodiment of the molded parts shown in FIGS. 9A-9E include the cover 901 with dimensions of about 6.0 cm×3.0 cm×0.2 cm and the base 902 with dimensions of about 5.0 cm×3.0 cm×0.2 cm to provide a cartridge 900 with dimensions of about 6.0 cm×3.0 cm×0.4 cm. In terms of ranges, the cartridge 900 optionally has a length of from 1 to 50 cm, e.g., from 5 to 15 cm, a width of from 0.5 to 15 cm, e.g., from 1 to 6 cm, and a thickness of from 0.1 to 2 cm, e.g., from 0.1 to 1 cm.

Processes for Target Analyte Detection in a Urine Sample

In preferred embodiments, the invention is a process for using a cartridge to determine the presence and/or concentration of a target analyte in a urine sample. The process may include introducing an unmetered fluid urine sample into the sample chamber 440 of the cartridge 400 through the sample entry port 445 (as shown in FIGS. 4-7). Capillary stop 565 prevents passage of the urine sample into conduit 510 at this stage, and conduit 440 is filled with the sample. Lid 435 is closed to prevent leakage of the sample from the cartridge. The cartridge may then be inserted into the reading device or apparatus 302, as shown in FIG. 3 and further disclosed in U.S. Pat. No. 5,821,399, which is incorporated herein by reference in its entirety. Insertion of the cartridge into the reading apparatus activates a mechanism, which punctures the fluid-containing package located at recess 475 when the package is pressed against spike 480. Fluid is thereby expelled into the conduits 485 and 490, arriving in sequence at the sensor region. The constriction 520 prevents further movement of fluid because residual hydrostatic pressure is dissipated by the flow of fluid via the conduit 585 into the waste chamber 560.

In a second step, operation of a pump means applies pressure to the air-bladder comprised of cavity 465, forcing air through the conduit 580 and into conduit 440 at a predetermined location. Capillary stop 565 delimits a metered portion of the original sample. While the sample is within sample chamber 440, it is preferably amended with a compound or compounds (e.g., urease and/or other enzymes, a water soluble protein, a buffer, scavengers, or a combination thereof, and/or antibodies to NGAL labeled with ALP) present initially as a dry coating or layer(s) on the inner surface of the chamber or conduits. The metered portion of the sample is then expelled through the capillary stop 565 by air pressure produced within air bladder comprised of cavity 465. The sample passes into the sensor conduit and into contact with the pair of electrodes and optionally the reference electrode located within the cutaway 605.

To promote binding of the analyte, e.g., NGAL to the electrodes, the sample containing the analyte may optionally be passed repeatedly over the electrodes in an oscillatory motion. Preferably, an oscillation frequency of between about 0.2 and 2 Hz is used, most preferably 0.7 Hz. After a period, e.g., 10 minutes, for the analyte/enzyme-antibody conjugate complex to bind to the electrodes, the sample may be ejected by further pressure applied to the air bladder comprised of cavity 465, and the sample passes to waste chamber 560. A wash step (in some embodiments a limited wash step) next removes non-specifically bound enzyme-conjugate from the sensor chamber. Fluid in the conduit 490 may be moved by a pump means, into contact with the sensors. The analysis fluid may be pulled slowly until a first air segment is detected at a conductivity sensor. Note that it may be an object of the invention that the rinsing is not sufficiently protracted or vigorous as to promote dissociation of specifically bound analyte or analyte/antibody-enzyme conjugate complex from the sensors.

Use of a cartridge with a closeable valve, preferably located between the sensor chamber and the waste chamber, is herein illustrated by a specific embodiment in which the concentration of NGAL is determined within a urine sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the electrodes/sensors through pads, and performs certain diagnostic tests. Insertion of the cartridge perforates the foil pouch introducing fluid into a conduit as previously described. The diagnostic tests determine whether fluid or sample is present in the conduits using the conductivity electrodes; determine whether electrical short circuits are present in the electrodes; and ensure that the sensor and ground electrodes are thermally equilibrated to, preferably, 37° C. prior to the analyte determination.

Various options exist for managing any temperature effect on an immunoassay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value Between t=1.5 and t=6.75, a metered portion of the urine sample, preferably between 4 and 200 μL, more preferably between 4 and 20 μL, and most preferably 7 μL, may be used to contact the electrodes/sensors as described above. The edges defining the forward and trailing edges of the sample are reciprocally moved over the sensor region at a frequency that is preferably between 0.2 to 2.0 Hz, and is most preferably 0.7 Hz. During this time, the amending reagent and enzyme-antibody conjugate dissolves within the sample, as previously described. The amount of enzyme-antibody conjugate that is coated onto the conduit is selected to yield a concentration when dissolved that is preferably higher than the highest anticipated NGAL concentration, and is most preferably six times higher than the highest anticipated NGAL concentration in the sample.

Between t=6.75 and t=10.0 the sample may be moved into the waste chamber via the closeable valve, preferably wetting the closeable valve and causing it to swell and close. The seal created by the closing of the valve permits the first pump means to be used to control motion of fluid from the sensor conduit to the post analysis conduit. After the valve closes and any remaining sample is locked in the post analysis conduit, the analyzer plunger retracts from the flexible diaphragm of the pump means creating a partial vacuum in the sensor conduit. This forces the analysis fluid through the small hole in the tape gasket and into a short transecting conduit in the base. The analysis fluid is then pulled further and the front edge of the analysis fluid is oscillated across the surface of the sensor chip in order to shear the sample near the walls of the conduit. A conductivity sensor on the sensor chip may be used to control this process. The efficiency of the process may be monitored using the amperometric sensors through the removal of unbound enzyme-antibody conjugate which enhances the oxidation current measured at the electrode when the enzyme substrate, p-aminophenyl phosphate is also present. The amperometric electrodes may be polarized to 0.06 V versus the silver chloride reference-ground electrode. In this embodiment, the fluid may be composed of a 0.1 M carbonate or diethanolamine buffer, at pH 9.8, with 1 mM MgCl2, 1.0 M NaCl, 10 mM p-aminophenylphosphate, and 10 μM (micromolar) NaI. The efficiency of the wash is optimally further enhanced by introduction into the fluid of one or more segments that segment the fluid within the conduit as previously described. Following removal of wash fluid from the sensor channel leaving a thin layer of fluid over the two sensors, measurement of each sensor response is recorded and the concentration of analyte determined as described above.

EXAMPLES

For purposes of illustration and not limitation, the following examples provide information on the performing an immunoassay on a urine sample and some aspects of the present invention including the amendment of the urine sample with urease and/or other enzymes, a water soluble protein, a buffer, scavengers, or combinations thereof.

Example 1 (i-STAT® Sandwich ELISA with cTnI in Urine)

Initial testing of urine as a sample matrix on the i-STAT platform was performed to compare cTnI spike results in urine and in whole blood. As a proof of concept, preexisting cTnI i-STAT ELISA technology and methodology was utilized prior to creating new NGAL methodologies.

cTnI i-STAT cartridges were warmed to room temperature from being refrigerated. Whole blood was drawn into a lithium heparin vacutainer, and midstream urine from the same donor was collected into a sterile vial (urine pH was ~6.9). A manufacturer's working calibrator of cTnI was used to spike whole blood or urine as appropriate (stock cTnI, 48.25 ng/mL; dilutions into whole blood or urine with final concentrations of 0.48, 1.86 and 9.65 ng/mL). It was determined that the donor's starting level of whole blood troponin was 0.0 ng/mL. Spiked samples were mixed on a nutator (Clay Adams, Parsippany, N.J.) at room temperature until time of use. Spiked whole blood and urine samples were loaded (20 μL) as replicates onto temperature equilibrated cartridges and after the test cycle was completed, chronoamperometric data was analyzed to calculate troponin levels. In addition, traces corresponding to motor motion, conductivity, reference and analyte current signals etc. were compared between whole blood and urine-based samples. No fluidic movement error codes during the run cycle indicated that the i-STAT system was capable of moving urine as a sample type within the cartridge conduits.

Figure 10:
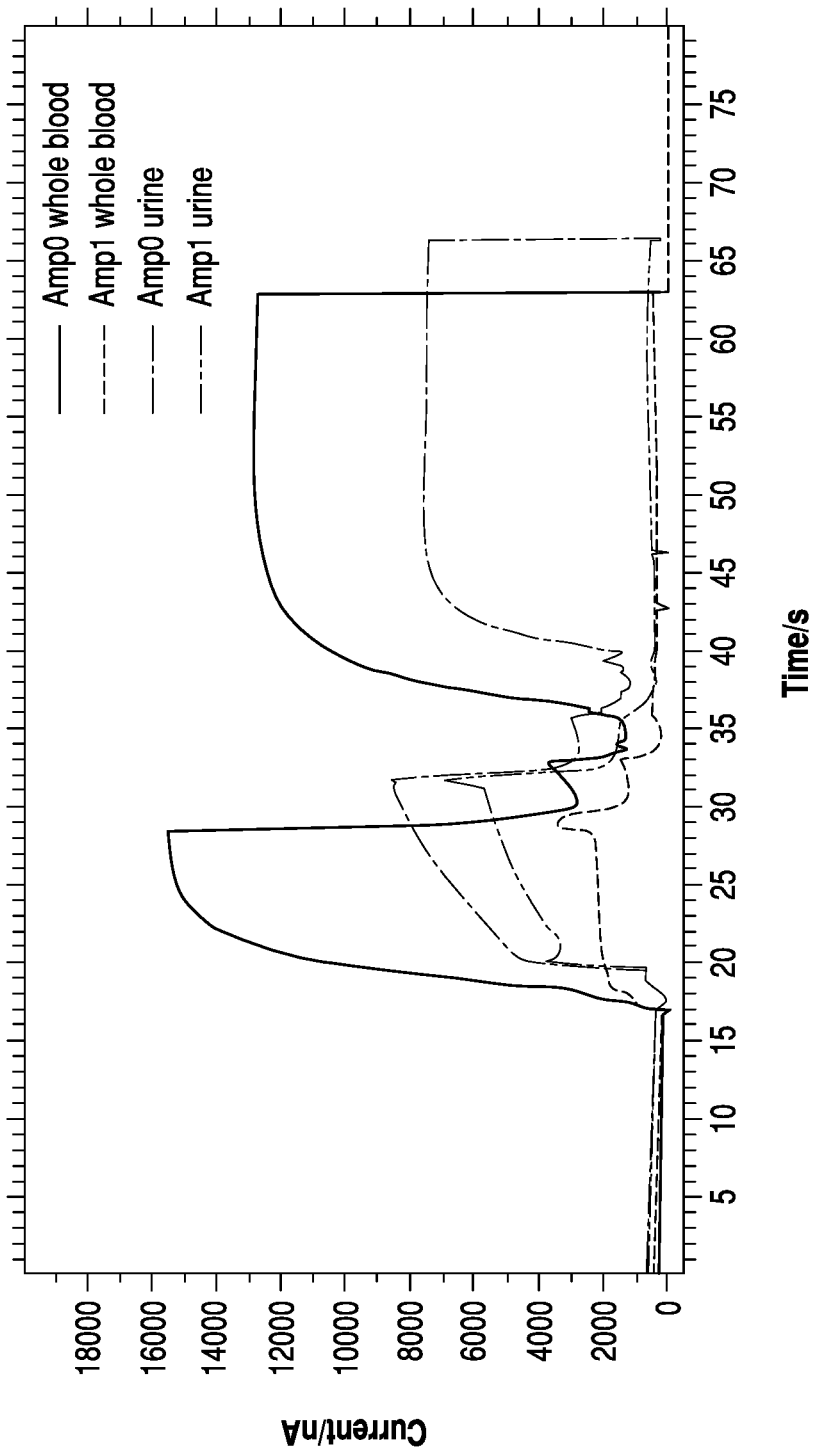
FIG. 10 shows chronoamperometric data of cTnI in whole blood and urine on i-STAT® in accordance with some aspects of the invention.

FIG. 10 illustrates a typical comparison of amperometric data from whole blood versus urine in this experiment. The signals generated from the urine were reproducibly almost half that of the whole blood samples. This data suggested an interference manifested by the presence of the urine sample. Without being bound by theory, possible mechanisms could be due to inadequate cTnI being recovered from the urine matrix during the ELISA steps or that the difference in conductivity between the sample types manifested an effect in signal or the urine contains interferents of the assay.

Figure 11:
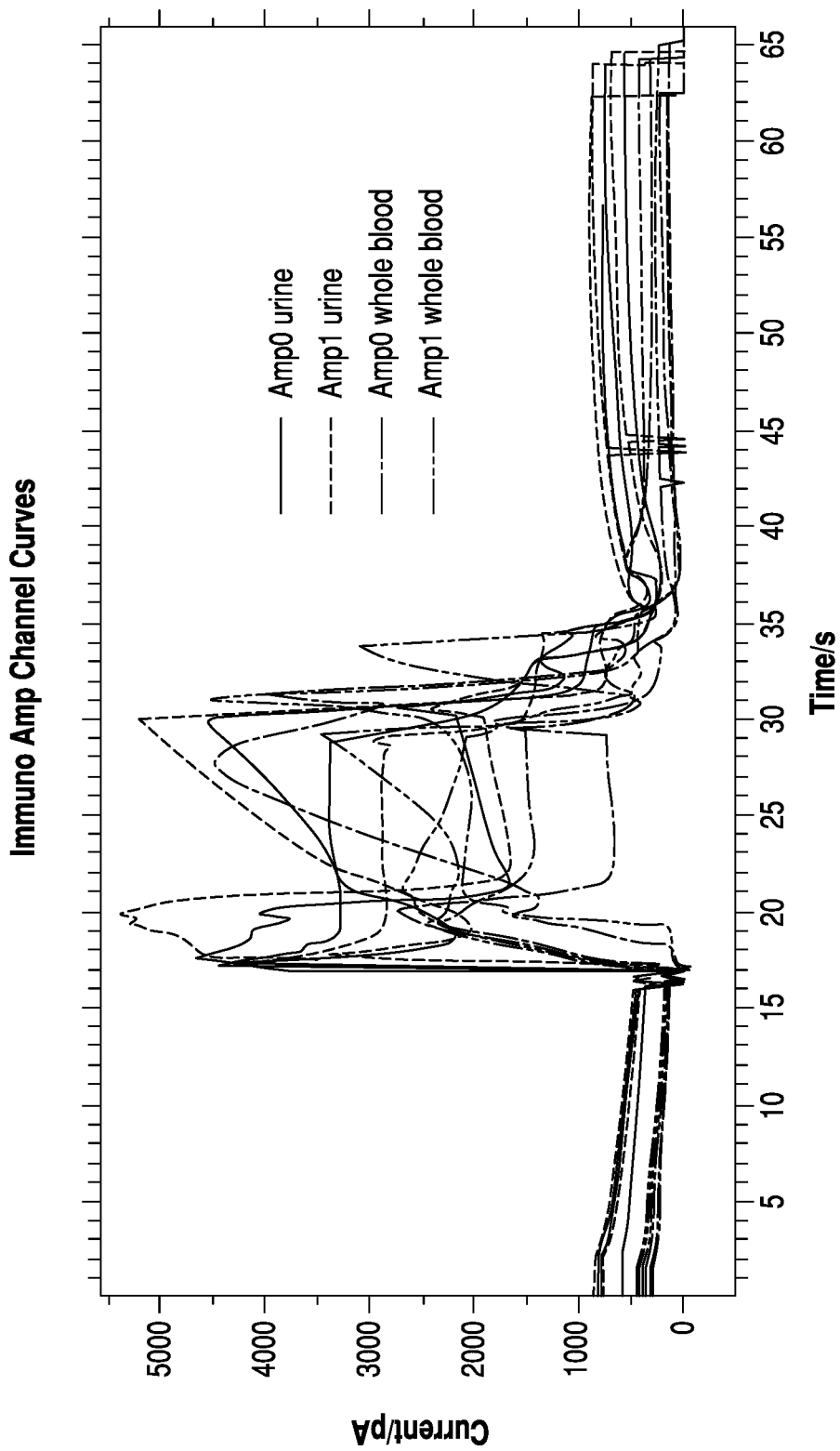
FIG. 11 shows chronoamperometric data of urine and whole blood background comparisons on i-STAT® showing analyte and reference currents for zero analyte cTnI samples in accordance with some aspects of the invention.

In addition, background current from both the analyte and reference electrodes was higher in urine samples than in the whole blood samples during capture. FIG. 11 is chronoamperometric data of urine and whole blood background comparisons on i-STAT showing analyte and reference currents for zero cTnI samples. Whole blood was represented by consistently lower traces while urine was represented by elevated signals. This background current interference occurred consistently throughout the test cycle on the urine reference sensor indicating that the cause may have originated from the sample when the blocking step should have occurred (reference sensor in the i-STAT immuno cartridges should capture human serum albumin from the blood; in addition, the cTnI analyte sensor beads also have anti-HSA capture antibody which should capture HSA and reduce background). In general, the HSA in the blood functions as an inherent blocking agent for the whole blood ELISA in the i-STAT system; serum albumin can also act as a buffer in solutions, especially where pH is at extremes (e.g., less than 3 and greater than 10). Due to the orders of magnitude difference in the albumin/protein concentration in whole blood versus urine (avg. 45 g/L vs 0.02 g/L, respectively), improper blocking of cartridge sensors and plastic from the urine matrix components likely led to increased background signals with urine.

Addition of casein, HSA or other albumin like BSA or recombinant human serum albumin into the urine sample as a pretreatment may mitigate this type of interference. Recombinant human serum albumin (rHSA) was selected for use since it is specific for the capture antibody being used in this example, and to reduce use of biohazardous material in the cartridge. Other interferents in urine (as compared to blood) can also play a role in background signal on both or either of the reference and analyte electrodes. For instance, certain B vitamins are known to be electroactive and may contribute to amperometric signals during the i-STAT cartridge cycle. Vitamin B scavengers may be incorporated in a urine pretreatment step as well in order to mitigate this type of electroactive interferent.

Urine was successfully used as a sample type on the i-STAT sandwich ELISA platform. Without being bound by theory, the background signal in urine seen on the reference and analyte sensors may be due to urine interferents or insufficient protein from urine, which can help in immunoassay systems.

Example 2 (i-STAT Sandwich Immunoassay with cTnI in rHSA-Amended Urine)

Commercially available cTnI i-STAT cartridges (Abbott Point of Care, Princeton, N.J.) were utilized in determining if addition of rHSA to urine samples would mitigate background current within the i-STAT immunoassay test cycle and increase analyte sensor current in urine.

A manufacturer's working calibrator of cTnI was used as described in Experiment 1 to spike urine as appropriate (stock cTnI, 48.25 ng/mL; dilutions into urine with final concentrations of 0.48, 1.86 and 9.65 ng/mL). HSA solution was made up as a 225 mg/mL stock in urine; dilution into the test samples was to 45 mg/mL, corresponding to the average HSA concentration found in whole blood). Spiked samples were mixed on a nutator (Clay Adams, Parsippany, N.J.) at room temperature for 10 minutes. 20 µL of spiked urine samples (+/−cTnI and +/−HSA) were loaded as replicates onto equilibrated cartridges and after the test cycle was completed, chronoamperometric data was analyzed to calculate troponin levels. In addition, traces corresponding to motor motion, conductivity, reference and analyte current signals etc. were reviewed. No fluidic movement error codes were logged during the run cycle, indicating that the i-STAT system was capable of moving urine +/−HSA as a sample type within the cartridge conduits. Background noise on reference and analyte sensors during ELISA capture was aptly mitigated by addition of HSA to 45 mg/mL. Adding HSA to urine also improved recovery of cTnI to almost the same level as whole blood spiked with an identical amount of troponin. Finally, adding HSA to urine spiked with low to medium levels of cTnI (up to ~2 ng/mL) mitigated background noise on the reference sensor during analysis, but had little effect with higher cTnI samples.

Example 3 (i-STAT Sandwich Immunoassay with NGAL in rHSA-Amended Urine)

Subsequent testing of urine as a sample type on the i-STAT platform was performed to compare rhNGAL (recombinant human) levels in urine+/−rHSA. In addition, this was undertaken to determine if rHSA could mitigate background current and increase analyte sensor current in rhNGAL-spiked urine. New NGAL sandwich ELISA reagents were created for this proof of concept in the i-STAT cartridge. This included using NGAL antibodies produced by Murine hybridoma cell lines 1-903-430 and 1-2322-455, which were each deposited with the American Type Culture Collection (hereinafter referred to as "ATCC"), 10801 University Blvd., Manassas, Va. 20110-2209, on Nov. 21, 2006. Cell line 1-903-430 was assigned ATCC Accession No. PTA-8026. Cell line 1-2322-455 was assigned ATCC Accession No. PTA-8024.

i-STAT immunosensors were printed with NGAL bead reagents and built into cartridges for testing. The cartridges were warmed to room temperature before testing. Midstream urine from the same donor as in Experiments 1 and 2 above was collected in a sterile tube (pH~7.0) and endogenous NGAL level was determined with an on-market NGAL ELISA Kit (BioPorto Diagnostics KIT037) in order to correct spiking values. For NGAL i-STAT cartridge proof of concept testing, rhNGAL protein was sourced from the ARCHITECT® (Abbott) rhNGAL calibrators. Urine was tested +/−rhNGAL and +/−rHSA (45 mg/mL). Whole blood was also tested with spiked amounts of rhNGAL and signals were generated, revealing that the i-STAT system could measure NGAL in whole blood. rhNGAL was spiked into urine samples at final concentrations of 0.5, 2 and 10 ng/mL. Spiked samples were mixed on a nutator (Clay Adams, Parsippany, N.J.) at room temperature for 10 minutes. NGAL antibody conjugate was spiked into the test samples to a final concentration of 1.2 µg/mL just prior to cartridge loading. A final volume of 20 µL spiked sample was added to the cartridge inlet to carry out the sandwich ELISA replicates.

Figure 12:
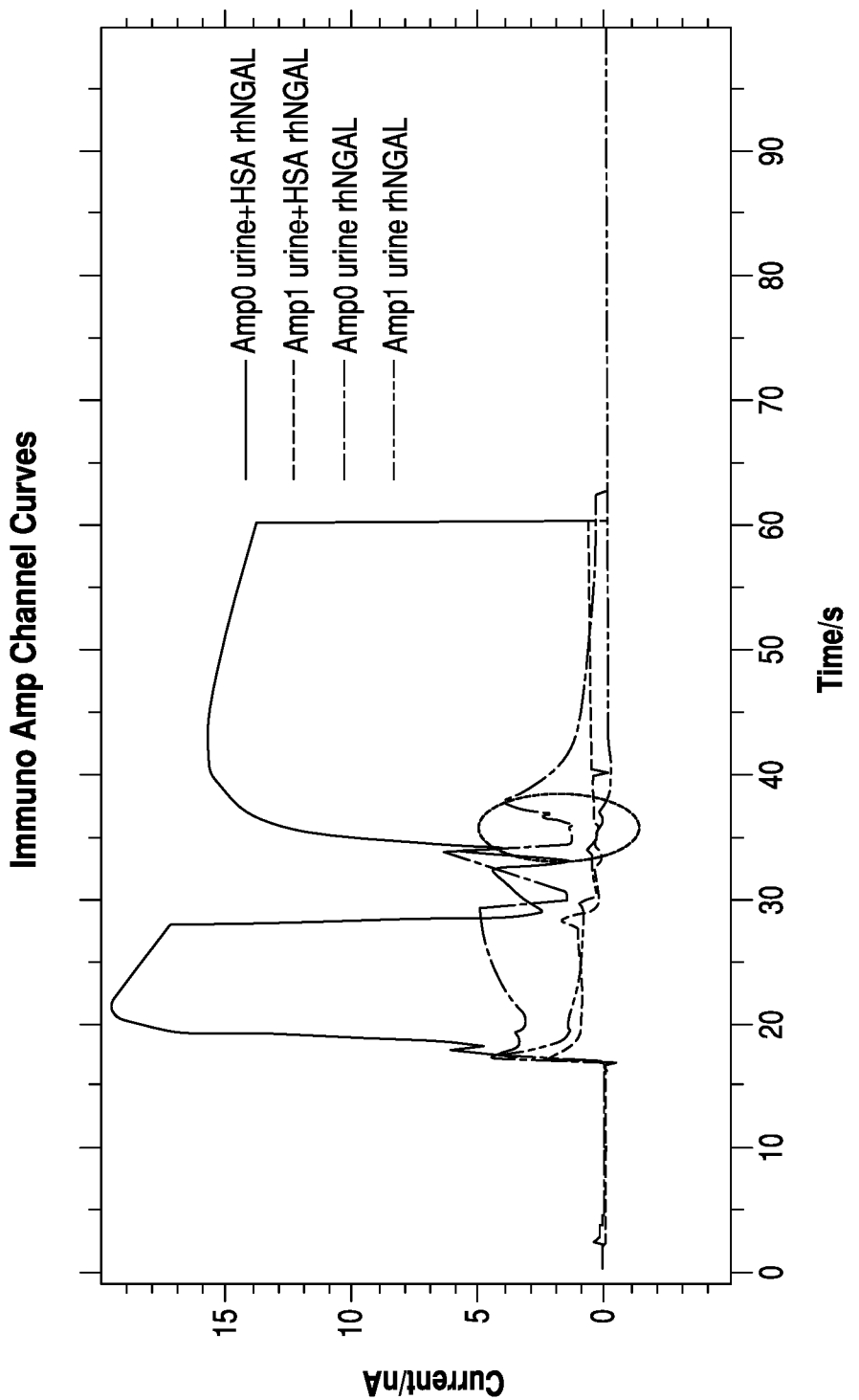
FIG. 12 shows chronoamperometric data for NGAL in urine with and without exogenous albumin in sample processed on i-STAT® in accordance with some aspects of the invention.
Figure 13:
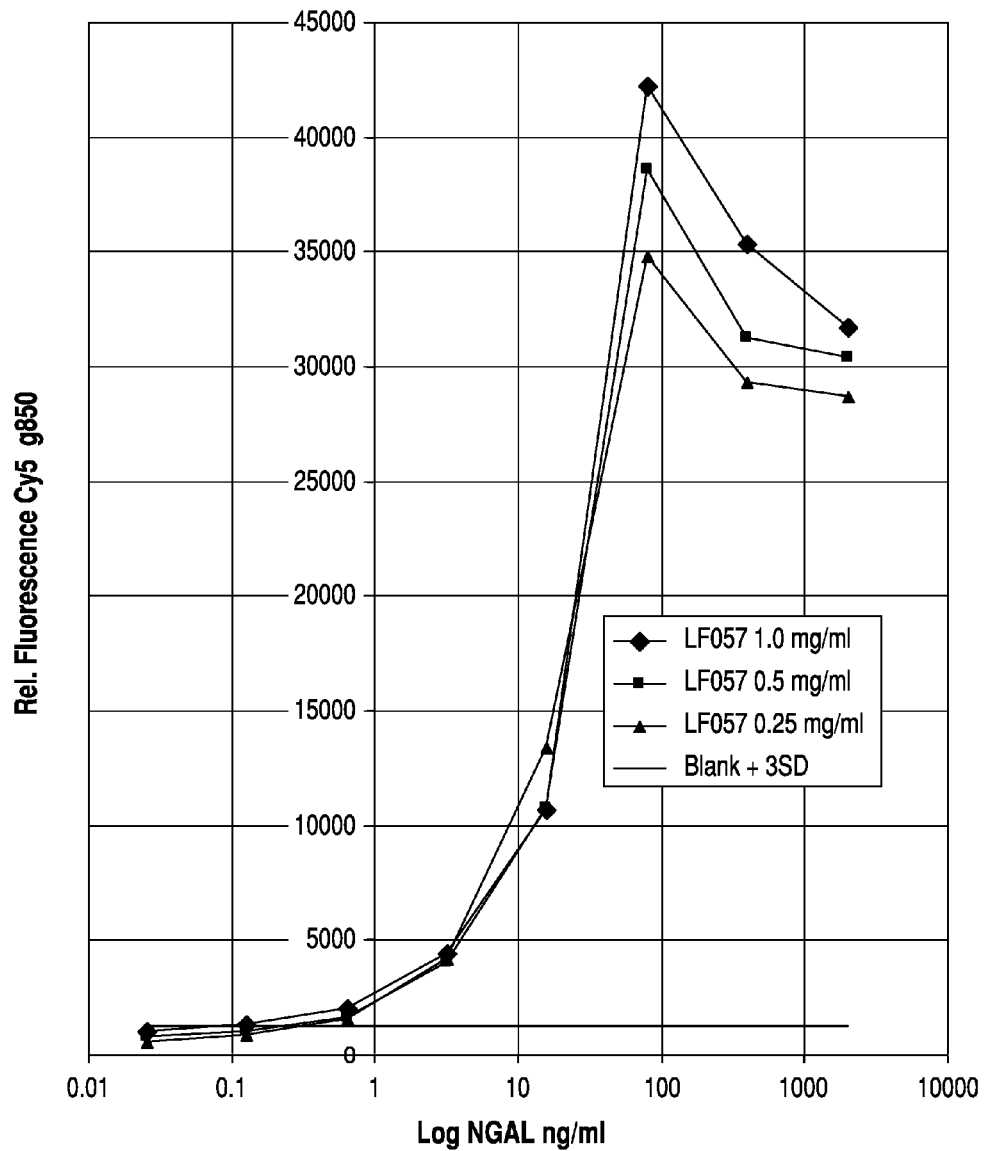
FIG. 13 shows a response curve for an NGAL sandwich ELISA in accordance with some aspects of the invention.

FIG. 12 is chronoamperometric data for NGAL in urine with and without exogenous albumin on the i-STAT platform. A linear relationship of amperometric signal and corresponding rhNGAL spikes was observed for low levels of rhNGAL (up to 10 ng/mL); this was the first evidence that rhNGAL can be measured using i-STAT cartridge technology/methodologies. Occasionally, there was a loss in conductivity between the reference/analyte/conductivity bar sensors (vertical oval in FIG. 12) leading to an interruption in signal generation during analysis. This was more pronounced at lower rhNGAL spike levels indicating that sensor wetup and maintenance was being compromised, likely due to low inherent matrix protein levels. This was supported by the finding that samples fortified with rHSA were able to avoid breaks in signal generation. But even with adjustment of reagent parameters, signal saturation began at around 100 ng/mL NGAL (FIG. 13), which indicates that not even the full normal range can be measured for this analyte using the current i-STAT paradigm. This is in contrast to the ARCHITECT uNGAL (urine NGAL) platform which covers a range from 10-6000 ng/mL (sandwich immunoassay with paramagnetic particles, autodilution and wash functions).

rhNGAL was measured in urine on the i-STAT platform using a traditional sandwich ELISA approach. Interruption of amperometric signal generation in low-level rhNGAL spike samples was mitigated by the introduction of exogenous rHSA (~45 mg/mL). The current immunoassay sandwich paradigm on the i-STAT system is insufficient to cover the dynamic range of NGAL in urine. A modification to the platform to include the capability for competitive immunoassay formats was tested next.

Example 4 (Competitive Immunoassay for NGAL in Buffer on Microplates)

Figure 14:
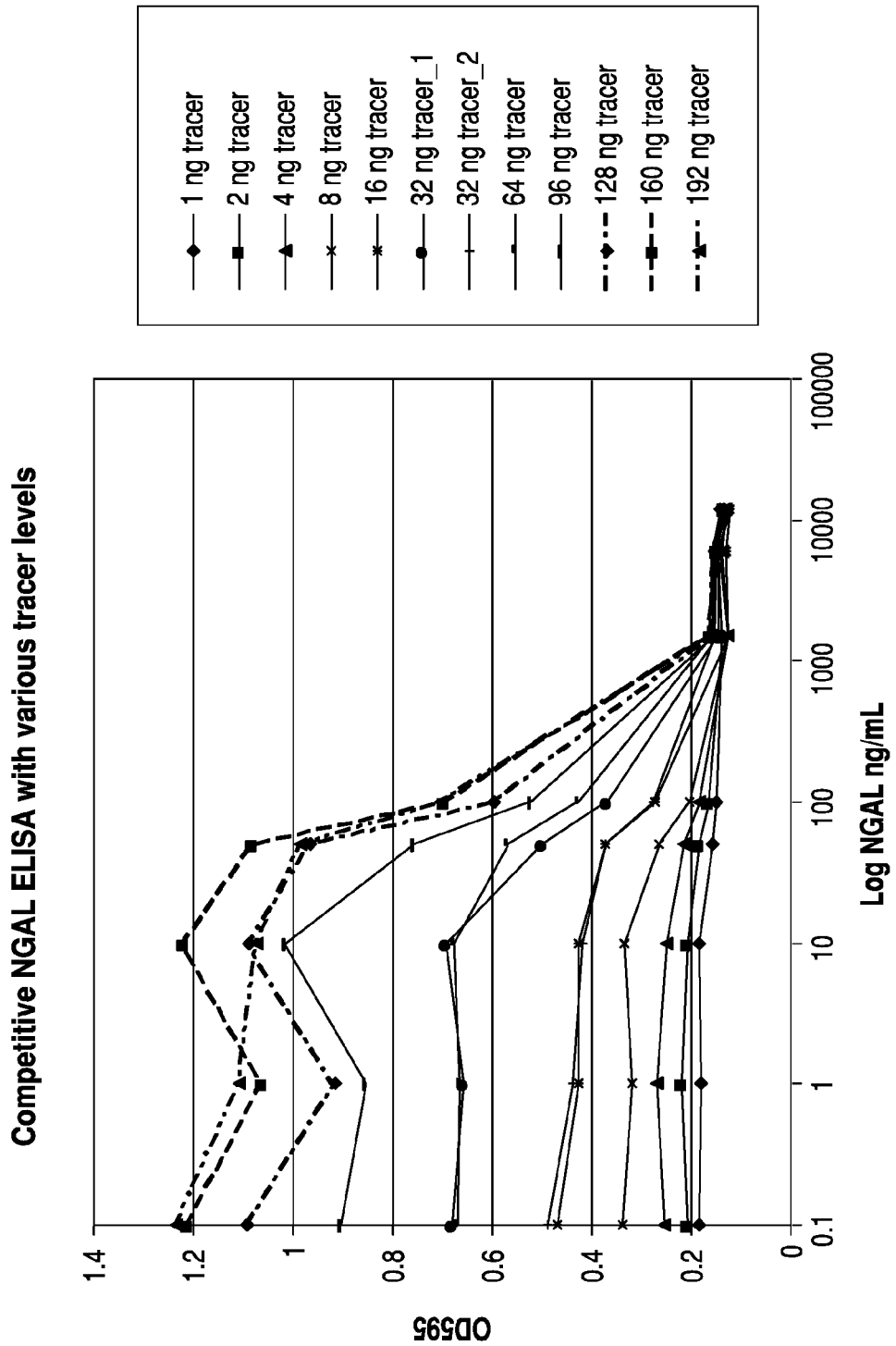
FIG. 14 shows a response curve for a competitive NGAL ELISA on microtitre plate in accordance with some aspects of the invention.

Off cartridge testing was employed to ascertain the tracer concentration needed in the i-STAT cartridge to effectively measure across the NGAL dynamic range described above using a competitive ELISA format. rhNGAL was spiked at various concentrations into a TB S/1% BSA, pH 8 solution (0.05 M Tris buffered saline NaCl—0.138 M; KCl—0.0027 M). Typical methodology was used to perform a plate ELISA. To coat the microtitre plate with capture antibody: 50 µL/well of 5 µg/mL capture antibody (LF68057) in bicarbonate buffer was left to incubate for 3 hours at room temperature. The wells were then washed with PBS several times before adding 1% BSA in TBS to block the wells for 2 hours at room temperature. TBS, pH 8.0 was used to wash the wells after blocking and the plate was blotted to remove excess moisture. 25 µL rhNGAL dilutions were mixed with an equal volume of ALP-NGAL tracer such that the final amount of tracer per test condition covered 1, 2, 4, 8, 16, 32, 64, 96, 128, 160, and 192 ng (final tracer diluted rhNGAL concs tested with each of the tracer amounts were 0, 1, 50, 100, 1500, 6000, 12000 ng/mL). Incubation proceeded at room temperature in a covered plate for 1 hour. Wells were washed 3 times with TBS, pH 8.0 then blotted dry; TMB substrate was prepared (Sigma Blue AP Substrate A plus B). 100 µL substrate was added to each well and colour development was allowed to take place. Measurements at 595 nm were taken and values were corrected for blank. Log NGAL concentration versus OD595 is plotted in FIG. 14. Good slope (sensitivity) was observed in the normal plasma range (40-110 ng/mL) and beyond. Tracer range between 32-128 ng per test seemed acceptable to cover the NGAL dynamic range; competitive ELISA using this tracer range with LF68057 capture antibody was tried next in urine on the i-STAT cartridge.

Example 5 (Competitive Immunoassay for NGAL in Urine on the i-STAT Cartridge)

Figure 15:
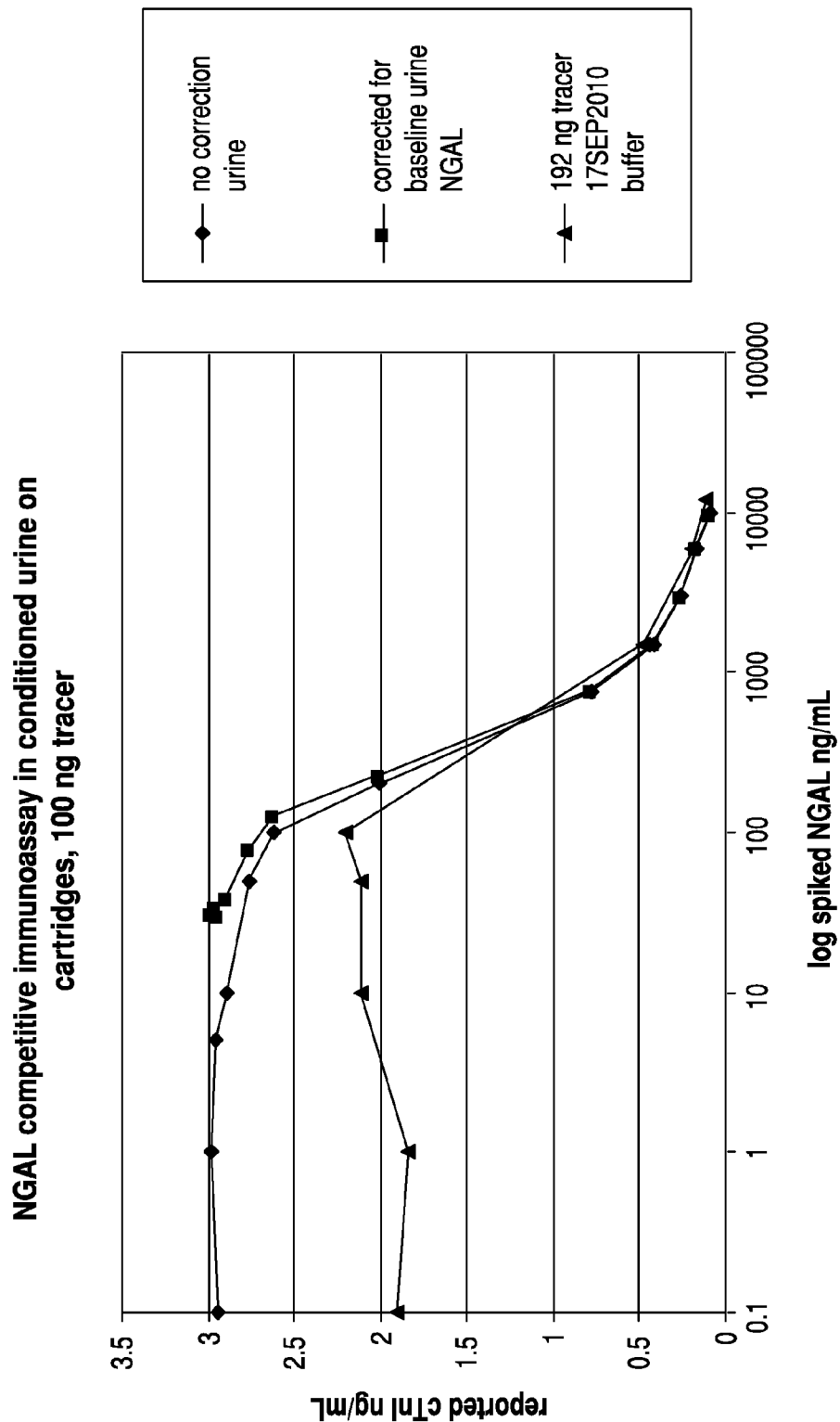
FIG. 15 shows a response curve for a competitive NGAL ELISA with spiked rhNGAL in conditioned urine in accordance with some aspects of the invention.

10 mM phosphate buffered saline (PBS) containing 0.01% Tween 20 (pH 7.2) was used as the assay buffer. The wash buffer was a 10 mM PBS containing 0.05% Tween 20 (pH 7.2). Using the LF68057 capture and HSA reference beads formulated as in the preferred embodiment below, sensors were printed and built into NGAL i-STAT cartridges for testing. rhNGAL (sourced from the ARCHITECT (Abbott) rhNGAL calibrators) was spiked into donor urine along with 45 mg/mL final concentration of rHSA and various tracer amounts (to test the range 32-128 ng per test urine sample; prepared as in Example 4). 20 µL of amended samples were loaded into cartridges for the competitive immunoassay test cycle (mixing and analysis conditions were kept similar to sandwich ELISA settings in the i-STAT; time to complex formation and conditions for wash and analysis cycle should be sufficient for both the sandwich and competitive formats with NGAL and ALP label). A tracer level of about 100 ng per 20 µL urine sample combined with the typical amount of capture antibody on the i-STAT bead preparations (~0.2 µg/mL with respect to sample volume; varying this allows for shifts in assay sensitivity) was found to be sensitive enough over the NGAL range to be used in the competitive assay on the i-STAT; no dilution of high concentration samples was necessary for the competitive format.

rhNGAL can be measured in urine by a competitive immunoassay format using the i-STAT system. Capture NGAL antibody linked to polystyrene beads, an alkaline phosphatase NGAL tracer, exogenous rHSA and an appropriate buffering solution were used in conjunction with the typical i-STAT cartridge shell to create a working urine NGAL competitive immunoassay which covers the appropriate NGAL range (FIG. 15).

Many types of immunoassay devices and processes have been described herein and the following jointly owned patents and applications are incorporated by reference for further understanding of these devices and processes. A disposable sensing device for successfully measuring analytes in a sample of blood is disclosed in U.S. Pat. No. 5,096,669. It employs a reading apparatus and a cartridge that fits into the reading apparatus for the purpose of measuring analyte concentrations in a sample of blood. Additionally, U.S. Pat. No. 7,723,099 describes an immunoassay device with an immuno-reference electrode; U.S. Pat. No. 7,682,833 describes an immunoassay device with improved sample closure; U.S. Patent Application Publication No. 2004/0018577 describes a multiple hybrid immunoassay; U.S. Patent Application Publication No. 2012/0295290 describes reducing interference from leukocytes in an immunoassay; U.S. Pat. No. 7,419,821 describes an apparatus and methods for analyte measurement and immunoassay; U.S. Pat. No. 8,084,272 addresses ameliorating interferences from heterophile antibodies; U.S. Patent Application Publication No. 2010/0167301 describes a device and methods for immunoassay using nucleotide conjugates; and U.S. Patent Application Publication No. 2012/0034684 describes a magnetic immunosensor that may be applicable for use with a urine sample, each of which is incorporated herein by reference in their entireties.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A method for performing an immunoassay for a target analyte in an amended urine sample, the method comprising:
providing a test device comprising: a first region comprising reagents; and a second region comprising a sensor comprising at least one electrode coated with a capture molecule capable of binding to the target analyte to form an immunocomplex, wherein the reagents comprise: (i) a water soluble protein for blocking non-specific binding of immunoglobulins at the at least one electrode, (ii) a buffer, and (iii) a scavenger for reducing non-specific current generation from electroactive species at the at least one electrode;
contacting a urine sample with the reagents in the first region to amend the urine sample such that a dissolved concentration of the water soluble protein within the amended urine sample is in a range of about 0.02 to 225 mg/mL;
contacting the amended urine sample with the second region to form the immunocomplex; and
determining a concentration of the target analyte within the amended urine sample by detecting the immunocomplex using the at least one electrode.

2. The method of claim 1, wherein:
the water soluble protein is recombinant or non-recombinant human serum albumin, porcine serum albumin, castor bean albumin, salmon serum albumin, bovine serum albumin, or a mixture thereof.

3. The method of claim 1, further comprising amending the urine sample with urease to reduce a urea concentration of the urine sample below a preselected urea threshold.

4. The method of claim 1, wherein the target analyte is neutrophil gelatinase-associated lipocalin (NGAL).

5. The method of claim 1, wherein:
the buffer adjusts a pH of the urine sample to within a preselected range; and
the buffer is selected from the group consisting of: glycine, 3-(N-morpholino) propanesulfonic acid (MOPS), tris(hydroxymethyl)aminomethane (Tris), tricine, acetate, borate, 2-(N-morpholino)ethanesulfonic acid (MES), and 2-[[1,3-dihydroxy-2-(hydroxymethyl)propan-2-yl]amino]ethanesulfonic acid (TES).

6. The method of claim 1, further comprising amending the urine sample with glutamine synthetase or any other urea cycle enzyme to consume ammonium.

7. The method of claim 1, further comprising amending the urine sample with a sequestering enzyme to reduce and sequester excess phosphate below a preselected phosphate threshold.

8. The method of claim 7, wherein the sequestering enzyme is adenylate kinase.

9. A method for performing an immunoassay for a target analyte in an amended urine sample, the method comprising:
 introducing an undiluted or partially diluted urine sample into a sample chamber of a cartridge through a sample entry port;
 amending the urine sample with reagents such that a dissolved concentration of water soluble protein within the amended urine sample is in a range of about 0.02 to 225 mg/mL, wherein the reagents comprise: (i) a water soluble protein for blocking non-specific binding of immunoglobulins at a sensor, (ii) a buffer, (iii) a conjugate molecule labeled with an enzyme capable of binding to the target analyte, and (iv) a scavenger for reducing non-specific current generation from electroactive species at at least electrode;
 contacting the amended urine sample with a sensor on the cartridge, wherein the sensor comprises a capture molecule and the at least one electrode, the a capture molecule is capable of binding to the target analyte bound to the conjugate molecule labeled with the enzyme to form an immunocomplex, and the at least one electrode is configured to detect the immunocomplex; and
 determining a concentration of the target analyte within the amended urine sample by detecting the immunocomplex using the at least one electrode.

10. The method of claim 9, wherein:
 the water soluble protein is recombinant or non-recombinant human serum albumin, porcine serum albumin, castor bean albumin, salmon serum albumin, bovine serum albumin, or a mixture thereof.

11. The method of claim 9, further comprising amending the urine sample with urease to reduce a urea concentration of the urine sample below a preselected urea threshold.

12. The method of claim 9, wherein the target analyte is neutrophil gelatinase-associated lipocalin (NGAL).

13. The method of claim 9, wherein:
 the buffer adjusts a pH of the urine sample to within a preselected range; and
 the buffer is selected from the group consisting of: glycine, 3-(N-morpholino) propanesulfonic acid (MOPS), tris(hydroxymethyl)aminomethane (Tris), tricine, acetate, borate, 2-(N-morpholino)ethanesulfonic acid (MES), and 2-[[1,3-dihydroxy-2-(hydroxymethyl)propan-2-yl]amino]ethanesulfonic acid (TES).

14. The method of claim 9, further comprising amending the urine sample with glutamine synthetase or any other urea cycle enzyme to consume ammonium.

15. The method of claim 9, further comprising amending the urine sample with a sequestering enzyme to reduce and sequester excess phosphate below a preselected phosphate threshold.

16. The method of claim 15, wherein the sequestering enzyme is adenylate kinase.

* * * * *